United States Patent
Heikenfeld

(10) Patent No.: US 11,129,554 B2
(45) Date of Patent: Sep. 28, 2021

(54) SWEAT MONITORING AND CONTROL OF DRUG DELIVERY

(71) Applicant: University Of Cincinnati, Cincinnati, OH (US)

(72) Inventor: Jason C. Heikenfeld, Cincinnati, OH (US)

(73) Assignee: University Of Cincinnati, Cincinnati, OH (US)

( * ) Notice: Subject to any disclaimer, the term of this patent is extended or adjusted under 35 U.S.C. 154(b) by 217 days.

(21) Appl. No.: 15/314,414

(22) PCT Filed: May 28, 2015

(86) PCT No.: PCT/US2015/032866
§ 371 (c)(1),
(2) Date: Nov. 28, 2016

(87) PCT Pub. No.: WO2015/184084
PCT Pub. Date: Dec. 3, 2015

(65) Prior Publication Data
US 2017/0095184 A1    Apr. 6, 2017

Related U.S. Application Data

(60) Provisional application No. 62/092,897, filed on Dec. 17, 2014, provisional application No. 62/023,233, filed on Jul. 11, 2014, provisional application No. 62/003,699, filed on May 28, 2014.

(51) Int. Cl.
| | |
|---|---|
| A61K 49/00 | (2006.01) |
| A61B 5/145 | (2006.01) |
| A61B 5/00 | (2006.01) |
| A61B 5/0531 | (2021.01) |
| A61M 37/00 | (2006.01) |
| A61N 1/04 | (2006.01) |
| A61N 1/32 | (2006.01) |

(52) U.S. Cl.
CPC ........ *A61B 5/14517* (2013.01); *A61B 5/0531* (2013.01); *A61B 5/14546* (2013.01); *A61B 5/4266* (2013.01); *A61B 5/4839* (2013.01); *A61B 5/6804* (2013.01); *A61B 5/6831* (2013.01); *A61M 37/0015* (2013.01); *A61N 1/0412* (2013.01); *A61N 1/0448* (2013.01); *A61N 1/327* (2013.01); *A61M 2037/0007* (2013.01); *A61M 2037/0023* (2013.01); *A61M 2230/005* (2013.01)

(58) Field of Classification Search
CPC ............ A61B 5/14517; A61B 5/14546; A61B 5/4266; A61B 5/4839; A61B 5/6804; A61B 5/6831; A61B 5/0531; A61M 37/0015; A61M 2037/0007; A61M 2037/0023; A61M 2230/005; A61N 1/0412; A61N 1/0448; A61N 1/327

USPC .......................................................... 424/9.2
See application file for complete search history.

(56) References Cited

U.S. PATENT DOCUMENTS

| | | |
|---|---|---|
| 4,190,060 A | 2/1980 | Greenleaf et al. |
| 4,542,751 A | 9/1985 | Webster et al. |
| 4,756,314 A | 7/1988 | Eckenhoff et al. |
| 4,820,263 A | 4/1989 | Spevak et al. |
| 5,036,861 A | 8/1991 | Sembrowich et al. |
| 5,050,604 A | 9/1991 | Reshef et al. |
| 5,140,985 A | 8/1992 | Schroeder et al. |
| 5,246,003 A | 9/1993 | DeLonzor |
| 5,438,984 A | 8/1995 | Schoendorfer |
| 5,556,789 A | 9/1996 | Goerlach-Graw et al. |
| 5,776,783 A * | 7/1998 | Kell ................... G01N 33/493 436/111 |
| 5,814,599 A | 9/1998 | Mitragotri et al. |
| 5,944,662 A | 8/1999 | Schoendorfer |

(Continued)

FOREIGN PATENT DOCUMENTS

| | | |
|---|---|---|
| CA | 2869469 A1 | 10/2013 |
| CN | 101489470 A | 7/2009 |

(Continued)

OTHER PUBLICATIONS

Vangiessen et al. J. Pharm. Sci. 1975, 64, 798-801.*

(Continued)

*Primary Examiner* — Michael G. Hartley
*Assistant Examiner* — Sean R Donohue
(74) *Attorney, Agent, or Firm* — Wood Herron & Evans LLP

(57) ABSTRACT

The concentration of an administered compound, such as a drug (D), in an organ or a bodily fluid, such as blood, is determined directly through detecting the drug (D) or its metabolites (DM) in sweat. The concentration may be determined indirectly by administering the drug (D) together with one or more tracer compounds (T, T2) or metabolites thereof (TM, T2M) or by detecting concentrations and trends of other analytes present in the body that react to the presence of the drug (D). By determining tracer concentration in sweat, the concentration of the drug (D) in blood or an organ can be determined. The tracer (T, T2) is a compound selected for ease of detection in sweat, known metabolic and solubility profiles that correspond to those of the drug (D), and safety of use. A smart transdermal delivery patch (300) is used to administer a dosage of drug to a wearer in coordination with at least one sweat sensor (324) reading conveying information about the wearer.

11 Claims, 4 Drawing Sheets

(56) References Cited

U.S. PATENT DOCUMENTS

| | | |
|---|---|---|
| 6,198,953 B1 | 3/2001 | Webster et al. |
| 6,256,533 B1 | 7/2001 | Yuzhakov et al. |
| 6,269,265 B1 | 7/2001 | Anderson |
| 6,299,578 B1 | 10/2001 | Kumik et al. |
| 6,592,529 B2 | 7/2003 | Marett |
| 6,666,821 B2 | 12/2003 | Keimel |
| 7,190,986 B1 | 3/2007 | Hannula et al. |
| 7,219,534 B2 | 5/2007 | Campbell |
| 7,378,054 B2 | 5/2008 | Karmali |
| 7,383,072 B2 | 6/2008 | Edmonson et al. |
| 7,384,396 B2 | 6/2008 | Samuels et al. |
| 7,749,445 B2 | 7/2010 | Masters |
| 7,813,780 B2 | 10/2010 | Shah et al. |
| 7,842,234 B2 | 11/2010 | Lauks et al. |
| 7,959,791 B2 | 6/2011 | Kjaer et al. |
| 8,125,539 B2 | 2/2012 | Takashima |
| 8,128,889 B2 | 3/2012 | Fujimoto et al. |
| 8,252,248 B2 | 8/2012 | Kramer |
| 8,391,946 B2 | 3/2013 | Sugenoya et al. |
| 8,565,850 B2 | 10/2013 | Martinsen et al. |
| 8,593,287 B2 | 11/2013 | Hayter et al. |
| 8,617,067 B2 | 12/2013 | Jain et al. |
| 9,133,024 B2 | 9/2015 | Phan et al. |
| 2002/0091312 A1 | 7/2002 | Berner et al. |
| 2003/0135100 A1 | 7/2003 | Kim et al. |
| 2003/0191376 A1 | 10/2003 | Samuels et al. |
| 2003/0201194 A1 | 10/2003 | Heller et al. |
| 2004/0249310 A1 | 12/2004 | Shartle et al. |
| 2004/0267189 A1 | 12/2004 | Mavor et al. |
| 2005/0069925 A1 | 3/2005 | Ford et al. |
| 2005/0106713 A1 | 5/2005 | Phan et al. |
| 2005/0177035 A1 | 8/2005 | Botvinick et al. |
| 2005/0192528 A1 | 9/2005 | Tapper |
| 2005/0197554 A1 | 9/2005 | Polcha |
| 2006/0004271 A1 | 1/2006 | Peyser et al. |
| 2006/0062852 A1 | 3/2006 | Holmes |
| 2006/0127964 A1 | 6/2006 | Ford et al. |
| 2006/0253011 A1 | 11/2006 | Edmonson et al. |
| 2006/0254341 A1 | 11/2006 | Campbell |
| 2007/0027383 A1 | 2/2007 | Peyser et al. |
| 2007/0032731 A1 | 2/2007 | Lovejoy et al. |
| 2007/0172424 A1* | 7/2007 | Roser ............ A61B 5/14546 424/9.1 |
| 2007/0179371 A1 | 8/2007 | Peyser et al. |
| 2008/0015494 A1 | 1/2008 | Santini et al. |
| 2008/0045816 A1 | 2/2008 | Jang et al. |
| 2008/0152592 A1* | 6/2008 | Rebec ............ A61B 5/145 424/9.2 |
| 2008/0154179 A1 | 6/2008 | Cantor |
| 2008/0286349 A1 | 11/2008 | Nomoto et al. |
| 2008/0306362 A1 | 12/2008 | Davis |
| 2009/0076345 A1 | 3/2009 | Manicka et al. |
| 2009/0204008 A1 | 8/2009 | Beilin |
| 2009/0270704 A1 | 10/2009 | Peyser et al. |
| 2010/0044224 A1 | 2/2010 | Kataky |
| 2010/0063372 A1 | 3/2010 | Potts et al. |
| 2010/0130843 A1 | 5/2010 | Caceres Galvez et al. |
| 2010/0132485 A1 | 6/2010 | Erez et al. |
| 2010/0198521 A1 | 8/2010 | Haick |
| 2011/0079521 A1 | 4/2011 | Revol-Cavalier |
| 2011/0118656 A1 | 5/2011 | Eckhoff et al. |
| 2011/0178380 A1 | 7/2011 | Chowdhury |
| 2011/0196283 A1 | 8/2011 | Imran et al. |
| 2011/0208458 A1 | 8/2011 | Pinter et al. |
| 2011/0275918 A1 | 11/2011 | Yamashita et al. |
| 2012/0004570 A1 | 1/2012 | Shimizu et al. |
| 2012/0028283 A1 | 2/2012 | Hoss et al. |
| 2012/0123220 A1 | 5/2012 | Iyer et al. |
| 2012/0165626 A1 | 6/2012 | Irina et al. |
| 2012/0209226 A1 | 8/2012 | Simmons et al. |
| 2012/0229661 A1 | 9/2012 | Sekiguchi et al. |
| 2012/0277697 A1 | 11/2012 | Haghooie |
| 2012/0285829 A1 | 11/2012 | Mount et al. |
| 2012/0317430 A1 | 12/2012 | Rahman et al. |
| 2012/0323097 A9 | 12/2012 | Chowdhury |
| 2013/0006079 A1 | 1/2013 | Feldman et al. |
| 2013/0010108 A1 | 1/2013 | Hashizume et al. |
| 2013/0013028 A1 | 1/2013 | Kriksunov et al. |
| 2013/0053668 A1 | 2/2013 | Lin |
| 2013/0079605 A1 | 3/2013 | Bandaru et al. |
| 2013/0099937 A1 | 4/2013 | Azimi |
| 2013/0108667 A1 | 5/2013 | Soikum et al. |
| 2013/0123595 A1 | 5/2013 | Currie et al. |
| 2013/0183399 A1 | 7/2013 | Blow et al. |
| 2013/0306491 A1 | 11/2013 | Briman et al. |
| 2013/0317333 A1 | 11/2013 | Yang et al. |
| 2014/0012114 A1 | 1/2014 | Zevenbergen et al. |
| 2014/0025000 A1 | 1/2014 | Currie et al. |
| 2014/0073892 A1* | 3/2014 | Randloev ............ A61B 5/14532 600/365 |
| 2014/0206977 A1 | 7/2014 | Bahney et al. |
| 2014/0275862 A1 | 9/2014 | Kennedy |
| 2014/0276220 A1 | 9/2014 | Briscoe et al. |
| 2014/0343371 A1 | 11/2014 | Sowers, II et al. |
| 2015/0057515 A1 | 2/2015 | Hagen |
| 2015/0112164 A1 | 4/2015 | Heikenfeld et al. |
| 2015/0112165 A1 | 4/2015 | Heikenfeld |
| 2016/0058354 A1 | 3/2016 | Phan et al. |
| 2016/0066828 A1 | 3/2016 | Phan et al. |
| 2016/0157768 A1 | 6/2016 | Braig et al. |

FOREIGN PATENT DOCUMENTS

| | | |
|---|---|---|
| EP | 0282349 A2 | 9/1988 |
| EP | 0453283 A1 | 10/1991 |
| EP | 0634215 A1 | 1/1995 |
| EP | 1500937 A1 | 1/2005 |
| EP | 1637889 A1 | 3/2006 |
| EP | 2551784 A1 | 1/2013 |
| JP | H07-77525 A | 3/1995 |
| JP | H08-504513 A | 5/1996 |
| JP | 2007503958 A | 3/2007 |
| JP | 2007532260 A | 11/2007 |
| JP | 2008505330 A | 2/2008 |
| JP | 200963597 A | 3/2009 |
| JP | 2009118420 A | 5/2009 |
| WO | 9011519 A1 | 10/1990 |
| WO | 9414062 A1 | 6/1994 |
| WO | 0014535 A1 | 3/2000 |
| WO | 01/88525 A1 | 11/2001 |
| WO | 2006133101 A2 | 12/2006 |
| WO | 2007097754 A1 | 8/2007 |
| WO | 2007146047 A1 | 12/2007 |
| WO | 2008083687 A1 | 7/2008 |
| WO | 2008095940 A1 | 8/2008 |
| WO | 2009004001 A1 | 1/2009 |
| WO | 2009052321 A2 | 4/2009 |
| WO | 2010/017578 A1 | 2/2010 |
| WO | 2011117952 A1 | 9/2011 |
| WO | 2013152087 A2 | 10/2013 |
| WO | 2013181436 A1 | 12/2013 |
| WO | 2014001577 A1 | 1/2014 |
| WO | 2014025430 A2 | 2/2014 |
| WO | 2015184072 A1 | 12/2015 |
| WO | 2015184097 A2 | 12/2015 |
| WO | 2016049019 A1 | 3/2016 |
| WO | 2016061362 A2 | 4/2016 |
| WO | 2016090189 A1 | 6/2016 |
| WO | 2016130905 A1 | 8/2016 |
| WO | 2016138087 A1 | 9/2016 |

OTHER PUBLICATIONS

Jamali Eur. J. Drug Metab. Pharmacokin. 1988, 1-9.*

European Patent Office, Supplemental European Search Report issued in European Application No. 15799514.3-1657 dated Dec. 7, 2017, 8 pages.

European Patent Office, Supplemental European Search Report issued in European Application No. 15799317.1-1657 dated Dec. 21, 2017, 9 pages.

European Patent Office, Partial European Search Report issued in European Application No. 15800043.0-115 dated Jan. 8, 2018, 13 pages.

(56) References Cited

OTHER PUBLICATIONS

International Searching Authority, Search Report and Written Opinion issued in International Application No. PCT/US2017/047574 dated Nov. 16, 2017, 14 pages.
International Searching Authority, Search Report and Written Opinion issued in International Application No. PCT/US2017/052651 dated Dec. 12, 2017, 14 pages.
Pike, Douglas J., et al., "Flow Cell Design for Effective Biosensing," Sensors, ISSN 1424-8220, Dec. 2012, vol. 13, pp. 58-70, www.mdpi.com/journal/sensors, 13 pages.
Sonner, Z., et al., "The microfluidics of the eccrine sweat gland, including biomarker partitioning, transport, and biosensing implications," Biomicrofluidics, vol. 9, pp. 031301-1-031301-19, CrossMark, 19 pages.
Agwah, Kenneth N., et al., "Pharmacokinetics and pharmacodynamics of the tetracyclines including glycylcyclines," Journal of Antimicrobial Chemotherapy, 2006, vol. 58, pp. 256-265, Advance Access Publication (10 pages).
Argatroban Injection, Package Insert for Argatroban Injection, "Highlights of Prescribing Information," Research Triangle Park, NC, GlaxoSmithKline, 2012 (22 pages).
Balant-Gorgia, Androniki E., et al., "Clinical Pharmacokinetics of Clompipramine," Clin. Pharmacokinet., vol. 20 (6), 1991, pp. 447-462 (16 pages).
Baxter, Roger, et al., "Comparison of Bactericidal Activity of Five Antibiotics against *Staphylococcus aureus*," Oxford Journals, The Journal of Infectious Diseases, vol. 161, No. 5, May 1990, pp. 1023-1025, Oxford University Press (4 pages).
Bertrand, Julie, et al., "Influence of pharmacogenetics on indinavir dispostion and short-term response in HIV patients initiating HAART," Eur J Clin Pharmacol., Jul. 22, 2010, vol. 65 (7), pp. 667-678 (17 pages).
Bockbrader, Howard N., et al., "Clinical Pharmacokinetics of Pregabalin in Healthy Volunteers," Journal of Clinical Pharmacology, 2010, vol. 50, pp. 941-950 (10 pages).
Buch, A.B., et al., "A Study of Pharmacokinetic Interaction Between Buspirone and Alprazolam at Steady State," J Clin Pharmacol, 1993, vol. 33, pp. 1104-1109 (6 pages).
Fonseca, Walter, et al., "Comparing Pharmacokinetics of Amoxicillin Given Twice or Three Times per Day to Children Older than 3 Months with Pneumonia," Antimicrobial Agents and Chemotherapy, Mar. 2003, vol. 47, No. 3, pp. 997-1001, American Society for Microbiology (5 pages).
Friedrich, Lawrance V., et al., "Aztreonam Pharmacokinetics in Burn Patients," Antimicrobial Agents and Chemotherapy, Jan. 1991, vol. 35, No. 1, pp. 57-61, American Society for Microbiology (5 pages).
Garcia, David A., et al., "Parenteral Anticoagulants: Antithrombotic Therapy and Prevention of Thrombosis, 9th ed: American College of Chest Physicians Evidence-Based Clinical Practice Guidelines," Chest, 2012, vol. 141 (2 Supplement), pp. e24S-e43S (20 pages).
Geller, David E., et al., "Pharmacokinetics and Bioavailability of Aerosolized Tobramycin in Cystic Fibrosis," Chest, vol. 122, No. 1, Jul. 2002, pp. 219-226 (8 pages).
Glazer, William M., et al., "The determination of the steady-state pharmacokinetic profile of fluphenazine decanoate by gas chromatography/mass spectrometry detection," Schizophrenia Research, 1992, vol. 8, pp. 111-117, Elsevier Science Publishers B.V. (7 pages).
Goodwin, Megan L., et al., "Antifungal serum concentration monitoring: an update," Journal of Antimicrobial Chemotherapy, 2008, vol. 61, pp. 17-25, Advance Access publication Nov. 12, 2007 (9 pages).
Hsu, Ann, et al., "Multiple-Dose Pharmacokinetics of Ritonavir in Human Immunodeficiency Virus-Infected Subjects," Antimicrobial Agents and Chemotherapy, May 1997, Vo. 41, No. 5, pp. 898-905, American Society for Microbiology (8 pages).
Hyland, R., et al., "Identification of the Cytochrome P450 Enzymes Involved in the N-Oxidation of Voriconazole," Drug Metabolism and Disposition, Jan. 2003, vol. 31, No. 5, pp. 540-547, The American Society for Pharmacology and Experimental Therapeutics (8 pages).
Kappelhoff, Bregt S., et al., "Pharmacokinetics of Nevirapine: Once-Daily Versus Twice-Daily Dosing in the 2NN-Study," HIV Clinical Trials, Sep. 2005, vol. 6(5), pp. 254-261, Thomas Land Publishers, Inc. (9 pages).
La Porte, C.J.L., et al., "Pharmacokinetics of Adjusted-Dose Lopinavir-Ritonavir Combined with Rifampin in Healthy Volunteers," Antimicrobial Agents and Chemotherapy, May 2004, vol. 48, No. 5, pp. 1553-1560, American Society for Microbiology (8 pages).
Lacy, Melinda K., et al., "Comparison of bactericidal activity after multidose administration of clarithromycin, azithromycin, and cefuroxime axetil aginst *Streptococcus pneumoniae*," International Journal of Antimicrobial Agents 10, 1998, pp. 279-283, Elsevier (5 pages).
Lai, Allen A., et al., "Time-course of interaction between carbamazepine and clonazepam in normal man," Clin. Pharmacol. Ther., Sep. 1978, vol. 24, pp. 316-323, The C.V. Mosby Co. (8 pages).
Marshall, William F., et al., "The Cephalosporins," Symposium on Antimicrobial Agents—Part V, Mayo Clin Proc, 1999, vol. 74, pp. 187-195 (9 pages).
McIlleron, Helen, et al., "Determinants of Rifampin, Isoniazid, Pyrazinamide, and Ethambutol Pharmacokinetics in a Cohort of Tuberculosis Patients," Antimicrobial Agents and Chemotherapy, Apr. 2006, vol. 50, No. 4, pp. 1170-1177, American Society for Microbiology (8 pages).
Medscape, "Drug, OTCs and Herbals | Medscape Reference," http://www.reference.medscapte.com/drugs, Accessed Mar. 2013 and Apr. 3, 2017 (1 page).
Mimaki, Takashi, "Clinical Pharmacology and Therapeutic Drug Monitoring of Zonisamide," Therapeutic Drug Monitoring, Dec. 1998, vol. 20(6), pp. 593-597, Lippincott Williams & Wilkins, Inc. (9 pages).
Molina, J-M., et al., "Pharmacokinetics of emtricitabine, didanosine andefavirenz administered once-daily for the treatment of HIV-infected adults (Pharmacokinetic substudy of the ANRS 091 trial)," HIV Medicine (2004), vol. 5, pp. 99-104, 2004 British HIV Association (6 pages).
Morse, Gene D., et al., "Multiple-Dose Pharmacokinetics of Delavirdine Mesylate and Didanosine in HIV-Infected Patients," Clin Drug Invest, 2003, pp. 323-328, vol. 23 (5), Adis Data Information BV (6 pages).
Munne P. International Programme on Chemical Safety Poisons Information Monograph 181, "Pharmacology and Toxicology," Published Apr. 1990, available at: http://www.inchem.org/documents/pims/pharm/pim181.htm#PartTitle:7.%20%20PHARMACOLOGY%20AND%20TOXICOLOGY, Accessed Oct. 2, 2009, pp. 14-18 (5 pages).
Nauta, Ernst H., et al., "Dicloxacillin and cloxacillin: Pharmacokinetics in healthy and hemodialysis subjects," Clinical Pharmacology and Therapeutics, vol. 20, No. 1, Feb. 13, 1976, pp. 98-108 (11 pages).
Ochs, Hermann R., et al., "Digitoxin Accumulation," Br. J. clin. Pharmac. (1982), vol. 14, pp. 225-229. The Macmillan Press Ltd 1982 (5 pages).
Ordonez Gallego, A., et al., "Oxycodone: a pharmacological and clinical review," Clin Transl Oncol, 2007, vol. 9, pp. 298-307 (10 pages).
Pippenger, C.E., et al., "Principles of Therapeutic Drug Monitoring," In: Wong Shy, ed. Therapeutic Drug Monitoring and Toxicology by Liquid Chromatography. Boca Raton, FL: CRC Press, 1985, pp. 11-36 (26 pages).
Purkins, L., et al., "Pharmacokinetics and Safety of Voriconazole following Intravenous-to Oral-Dose Escalation Regimens," Antimicrobial Agents and Chemotherapy, Aug. 2002, vol. 46, No. 8, pp. 2546-2553, American Society for Microbiology (8 pages).
Purkins, Lynn, et al., "The pharmacokinetics and safety of intravenous voriconazole—a novel wide-spectrum antifungal agent," Br J Clin Pharmacol, 2003, vol. 56, pp. 2-9, Blackwell Publishing Ltd (8 pages).

(56) References Cited

OTHER PUBLICATIONS

Ratjen, F., et al., "Pharmacokinetics of inhaled colistin in patients with cystic fibrosis," Journal of Antimicrobial Chemotherapy, 2006, vol. 57, pp. 306-311 (6 pages).

Remmel, Rory P., et al., "Simultaneous Assay of Felbamate plus Carbamazepine, Phenytoin, and Their Metabolites by Liquid Chromatography with Mobile Phase Optimization," Therapeutic Drug Monitoring, 1990, vol. 12, pp. 90-96, Raven Press, Ltd., New York (7 pages).

Rosenfeld, W.E., et al., "Comparison of the Steady-State Pharmacokinetics of Topiramate and Valproate in Patients with Epilepsy During Monotherapy and Concomitant Therapy," Epilepsia, 1997, vol. 38(3), pp. 324-333, Lippincott-Raven Publishers, Philadelphia (10 pages).

Ruslami, Rovina, et al., "Pharmacokinetics and Tolerability of a Higher Rifampin Dose versus the Standard Dose in Pulmonary Tuberculosis Patients," Antimicrobial Agents and Chemotherapy, Jul. 2007, vol. 51, No. 7, pp. 2546-2551, American Society for Microbiology (6 pages).

Rythmol, Package Insert for Rythmol, "Highlights of Prescribing Information," Reliant Pharmaceuticals Inc., 2004 (24 pages).

Sadler, Brian M., et al., "Pharmacokinetic and Pharmacodynamic Study of the Human Immunodeficiency Virus Protease Inhibitor Amprenavir after Multiple Oral Dosing," Antimicrobial Agents and Chemotherapy, Jan. 2001, vol. 45, No. 1, pp. 30-37, American Society for Microbiology (8 pages).

Silverstein, Jeffrey H., et al., "An Analysis of the Duration of Fentanyl and Its Metabolites in Urine and Saliva," Anesth Analg, 1993, vol. 76:6, pp. 618-621, The International Anesthesia Research Society (4 pages).

Sobue, Satoshi, et al., "Pharmacokinetics of fosfluconzaole and fluconazole following multiple intravenous administration of fosfluconazole in healthy male volunteers," British Journal of Clinical Pharmacology, 2004, vol. 58:1, pp. 20-25, Blackwell Publishing Ltd. (6 pages).

Ti, Teow-Yee, et al., "Disposition of Intravenous Metronidazole in Asian Surgical Patients," Antimicrobial Agents and Chemotherapy, Oct. 1996, vol. 40, No. 10, pp. 2248-2251, American Society for Microbiology (4 pages).

Viracept, Package Insert for Viracept, "Highlights of Prescribing Information," Agouron Pharmaceuticals, 2008 (27 pages).

Von Hentig, Nils, et al., "Pharmacokinetics of Saquinavir, Atazanavir, and Ritonavir in a Twice-Daily Boosted Double-Protease Inhibitor Regimen," Antimicrobial Agents and Chemotherapy, Apr. 2007, vol. 51, No. 4, pp. 1431-1439, American Society for Microbiology (9 pages).

Wilens, Timothy E., et al., "Fluoxetine Pharmacokinetics in Pediatric Patients," Journal of Clinical Psychopharmacology, 2002, vol. 22, No. 6, pp. 568-575, Lippincott Williams & Wilkins, Inc. (8 pages).

Wong, Steven H.Y., "Therapeutic Drug Monitoring and Toxicology by Liquid Chromatography," Chromatographic Science Series, 1985, vol. 32, Chapter 2 "Principles of Therapeutic Drug Monitoring" by C.E. Pippenger, Marcel Dekker, Inc., New York and Basel (34 pages).

Yamamoto, Takatsugu, et al., "Pharmacokinetic Characteristics of Minocycline in Debilitated Elderly Patients," American Journal of Therapeutics, 1999, vol. 6, pp. 157-160 (4 pages).

Zyprexa Relprevv, Package Insert for Zyprexa Relprevv, "Highlights of Prescribing Information," Eli Lilly and Company, 2008 (27 pages).

Australian Patent Office, Patent Examination Report No. 1 issued in Australian Application No. 2013243541 dated Nov. 25, 2016, 4 pages.

Australian Patent Office, Notice of Acceptance for Patent Application issued in Australian Application No, 2013243541 dated Mar. 23, 2017 (3 pages).

Chinese Patent Office, First Office Action issued in Chinese Application No. 201380028053.8 dated Dec. 21, 2015, 4 pages.

Chinese Patent Office, Second Office Action issued in Chinese Application No. 201380028053.8 dated Sep. 20, 2016, 8 pages (including English language translation).

Chinese Patent Office, Third Office Action issued in Chinese Application No. 201380028053.8 dated Mar. 20, 2017, 17 pages (including English language translation).

European Patent Office, Written Opinion of the International Searching Authority / International Preliminary Report on Patentability dated Oct. 16, 2014 (14 pages).

European Patent Office, Partial European Search Report issued in European Application No. 16203346.8-1657 dated Mar. 24, 2017, 7 pages.

Fu et al., "Controlled Reagent Transport in Disposable 2D Paper Networks", The Royal Society of Chemistry 2010, Lab Chip, 2010, 10, 918-920.

International Bureau, Notification Concerning Transmittal of International Preliminary Report on Patentability issued in International Application No. PCT/US13/35092 dated Oct. 7, 2014, 14 pages.

International Searching Authority, Invitation to Pay Additional Fees and, Where Applicable, Protest Fee, and Communication Relating to the Results of the Partial International Search, issued in International Application No. PCT/US13/35092 dated Aug. 26, 2013, 9 pages.

International Searching Authority, Invitation to Pay Additional Search Fees and, Where Applicable, Protest Fee, and Communication Relating to the Results of the Partial International Search, issued in International Application No. PCT/US2014/061083 dated Dec. 15, 2014, 6 pages.

International Searching Authority, Invitation to Pay Additional Search Fees and, Where Applicable, Protest Fee, and Communication Relating to the Results of the Partial International Search, issued in International Application No. PCT/US2015/032843 dated Aug. 18, 2015, 2 pages.

International Searching Authority, Invitation to Pay Additional Search Fees and, Where Applicable, Protest Fee, and Communication Relating to the Results of the Partial International Search, issued in International Application No. PCT/US2015/032866 dated Aug. 31, 2015, 2 pages.

International Searching Authority, Invitation to Pay Additional Search Fees and, Where Applicable, Protest Fee, and Communication Relating to the Results of the Partial International Search, issued in International Application No. PCT/US2015/032893 dated Aug. 31, 2015, 2 pages.

International Searching Authority, Invitation to Pay Additional Search Fees and, Where Applicable, Protest Fee, and Communication Relating to the Results of the Partial International Search, issued in International Application No. PCT/US2015/040113 dated Dec. 1, 2015, 2 pages.

International Searching Authority, Search Report and Written Opinion issued in International Application No. PCT/US2014/061098 dated Dec. 19, 2014, 13 pages.

International Searching Authority, Search Report and Written Opinion issued in International Application No. PCT/US2014/061083 dated Mar. 31, 2015, 18 pages.

International Searching Authority, Search Report and Written Opinion issued in International Application No. PCT/US2015/032830 dated Aug. 14, 2015, 9 pages.

International Searching Authority, Search Report and Written Opinion issued in International Application No. PCT/US2015/032843 dated Oct. 26, 2015, 11 pages.

International Searching Authority, Search Report and Written Opinion issued in International Application No. PCT/US2015/032893 dated Nov. 13, 2015, 14 pages.

International Searching Authority, Search Report and Written Opinion issued in International Application No. PCT/US2015/032866 dated Nov. 19, 2015, 12 pages.

International Searching Authority, Search Report and Written Opinion issued in International Application No. PCT/US2015/051439 dated Dec. 28, 2015, 7 pages.

International Searching Authority, Search Report and Written Opinion issued in International Application No. PCT/US2015/040113 dated Feb. 4, 2016, 13 pages.

(56) References Cited

OTHER PUBLICATIONS

International Searching Authority, Search Report and Written Opinion issued in International Application No. PCT/US16/18635 dated May 6, 2016, 12 pages.
International Searching Authority, Search Report and Written Opinion issued in International Application No. PCT/US16/17726 dated May 12, 2016, 9 pages.
International Searching Authority, Search Report and Written Opinion issued in International Application No. PCT/US16/50928 dated Sep. 9, 2016, 8 pages.
International Searching Authority, Search Report and Written Opinion issued in International Application No. PCT/US16/43862 dated Oct. 19, 2016, 14 pages.
International Searching Authority, Search Report and Written Opinion issued in International Application No. PCT/US16/59392 dated Oct. 28, 2016, 13 pages.
Japanese Patent Office, Office Action issued in Japanese Application No. 2015-504702 dated Jan. 20, 2017, 7 pages (including English language translation).
Stoppa, Matteo, et. al., "Wearable Electronics and Smart Tectiles: A Critical Review," Sensors, 2014, pp. 11957-11992, vol. 14 (36 pages).
International Searching Authority, Search Report and Written Opinion issued in related International Application No. PCT/US2017/013453 dated May 18, 2017, 14 pages.
International Searching Authority, Search Report and Written Opinion issued in related International Application No. PCT/US2017/039421 dated Sep. 6, 2017, 10 pages.
International Searching Authority, Search Report and Written Opinion issued in related International Application No. PCT/US2017/040588 dated Sep. 25, 2017, 11 pages.
European Patent Office, Official Communication for EP Application No. 13 718 933.8-1101 dated Feb. 14, 2018 (5 pages).
European Patent Office, Extended European Search Report issued in European Application No. 15819306.0-1115 dated Feb. 9, 2018 (9 pages).
International Searching Authority, Search Report and Written Opinion issued in International Application No. PCT/US2017/067495 dated Mar. 1, 2018, 10 pages.
International Searching Authority/U.S. International Search Report and Written Opinion issued in corresponding PCT Application No. PCT/US2016/059392, dated Feb. 15, 2017 (12 pages).
European Patent Office, Extended Search Report issued in European Application No. 15844313.5 dated Mar. 15, 2018, 15 pages.
De Jong, J. et al., "Membranes and microfluidics: a review," Lab Chip, 2006, 6, 1125-1139 (15 pages).
Yamazaki, T. et al., "Smart Integrated Sensor for Multiple Detections of Glucose and L-Lactate Using On-Chip Electrochemical System," Journal of Sensors, vol. 2011, Article ID 190284, doi:10.1155/2011/190284, Accepted Apr. 26, 2011, 7 pages.
European Patent Office, Extended European Search Report issued for European Patent Application No. 15800043.0, dated Apr. 16, 2018, 11 pages.
European Patent Office, Extended European Search Report issued in corresponding European Application No. 15800539.7, dated Aug. 17, 2018 (6 pages).

* cited by examiner

SWEAT MONITORING AND CONTROL OF DRUG DELIVERY

CROSS-REFERENCE TO RELATED APPLICATIONS

This application is the U.S. National phase application of PCT Application No. PCT/US2015/032866, entitled "SWEAT MONITORING AND CONTROL OF DRUG DELIVERY", filed May 28, 2015, claims the benefit of U.S. Provisional Application No. 62/003,699 entitled "SWEAT MONITORING OF PRODUCT DELIVERY AND DOSAGE", filed May 28, 2014, No. 62/023,233 entitled "SWEAT SENSOR WITH CHRONOLOGICAL ASSURANCE", filed Jul. 11, 2014, and No. 62/092,897 entitled "SWEAT MONITORING OF PRODUCT DELIVERY AND DOSAGE", filed Dec. 17, 2014, the disclosures of which are hereby incorporated by reference herein in their entirety.

BACKGROUND OF THE INVENTION

Sweat sensing technologies have enormous potential for applications ranging from athletics, to neonates, to pharmacological monitoring, to personal digital health, to name a few applications. Sweat contains many of the same biomarkers, chemicals, or solutes that are carried in blood and can provide significant information enabling one to diagnose ailments, health status, toxins, performance, and other physiological attributes even in advance of any physical sign. Furthermore, sweat itself, the action of sweating, and other parameters, attributes, solutes, or features on, near, or beneath the skin can be measured to further reveal physiological information.

If sweat has such significant potential as a sensing paradigm, then why has it not emerged beyond decades-old usage in infant chloride assays for Cystic Fibrosis or in illicit drug monitoring patches? In decades of sweat sensing literature, the majority of medical literature utilizes the crude, slow, and inconvenient process of sweat stimulation, collection of a sample, transport of the sample to a lab, and then analysis of the sample by a bench-top machine and a trained expert. This process is so labor intensive, complicated, and costly that in most cases, one would just as well implement a blood draw since it is the gold standard for most forms of high performance biomarker sensing. Hence, sweat sensing has not emerged into its fullest opportunity and capability for biosensing, especially for continuous or repeated biosensing or monitoring. Furthermore, attempts at using sweat to sense "holy grails" such as glucose have not yet succeeded to produce viable commercial products, reducing the publically perceived capability and opportunity space for sweat sensing.

Of all the other physiological fluids used for bio monitoring (e.g., blood, urine, saliva, tears), sweat has arguably the most variable sampling rate as its collection methods and variable rate of generation both induce large variances in the effective sampling rate. Sweat is also exposed to numerous contamination sources, which can distort the effective sampling rate. The variable sampling rate creates a challenge in providing chronological assurance, especially so in continuous monitoring applications.

Detection of drug compounds, particularly a concentration over time in bodily fluids, is complex and difficult. Continuous detection and monitoring by blood draw is undesirable. Saliva is inconvenient and prone to contamination. Chronologically sensing urine would require a catheter. Tears are also difficult to access regularly and ergonomically. Therefore, alternate methods of detection are needed. Once these methods are in hand, non-invasive sensing and drug delivery control becomes a possibility with numerous potential applications.

Many of the drawbacks stated above can be resolved by creating novel and advanced interplays of chemicals, materials, sensors, electronics, microfluidics, algorithms, computing, software, systems, and other features or designs, in a manner that affordably, effectively, conveniently, intelligently, or reliably brings sweat sensing technology into intimate proximity with sweat as it is generated. With such a new invention, sweat sensing could become a compelling new paradigm as a biosensing platform.

SUMMARY OF THE INVENTION

The concentration in a bodily fluid of a delivered solute such as a drug administered to an individual is detected indirectly by co-administering to the patient a known amount of a tracer compound that predictably emerges in sweat, and is easily detectable or has a metabolite that is easily detectible in sweat and/or is detected indirectly by monitoring the ratios and concentration trends of the drug, its metabolites, and naturally-occurring analytes in sweat that are correlated to the presence of the delivered solute in the body. With the detection and monitoring of the delivered solute using an individual's sweat, the drug delivery system can then use sweat sensor data and algorithms to continuously control the delivery of the solute through a smart transdermal delivery device.

BRIEF DESCRIPTION OF THE DRAWINGS

The objects and advantages of the present invention will be further appreciated in light of the following detailed descriptions and drawings in which.

DEFINITIONS

Figure 1:
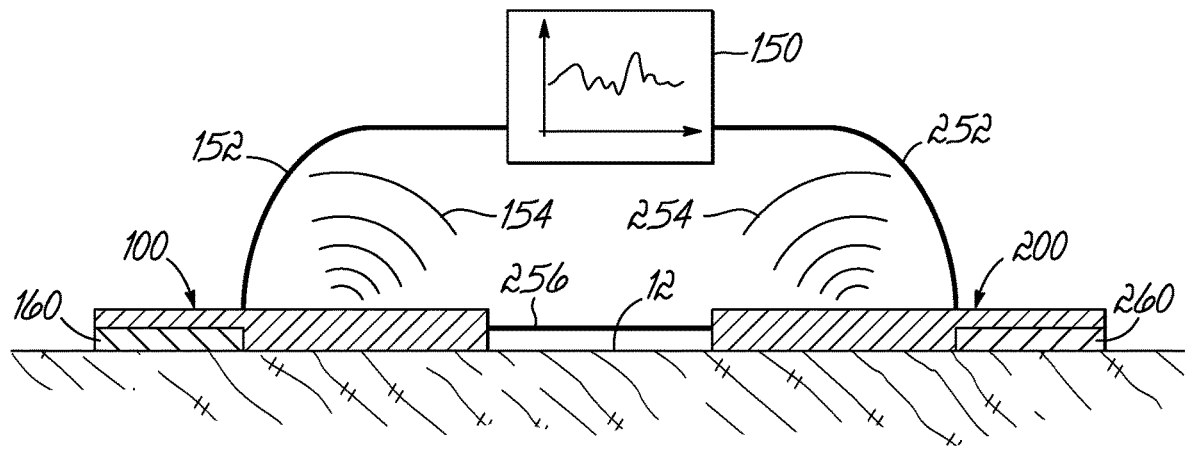
FIG. 1 is a schematic of a sweat sensor device and a smart transdermal delivery device in communication with each other and with a reader device.

As used herein, "delivered solute" means any substance that is at least partially soluble in plasma (blood), tissue or sweat and that may be delivered into the human body. For example, any drug, fluid, vitamin, inert substance, salt, sugar, molecule, grain, or other suitable substance or compound may be a delivered solute.

As used herein, "analyte" means any substance can provide meaningful measurements of physiological importance, and that is present in sweat.

As used herein, "sweat sensor data" means all of the information collected by sweat sensor(s) and communicated via the device to a user or a data aggregation location.

As used herein, "correlated aggregated sweat sensor data" means sweat sensor data that has been collected in a data aggregation location and correlated with outside information such as time, temperature, weather, location, user profile, other sweat sensor data, or any other relevant data.

As used herein, "tracer compound" or "tracer" means a compound having a known co-relationship between the tracer compound's concentration in sweat with the concentration of a primary drug in blood or an organ. The tracer may be more readily detectable in sweat than the drug itself, in a lower concentration, non-toxic, and less or differently bioactive than the primary drug.

As used herein, "tracer profile" means the collection of sweat sensor data on analytes that indicate the concentration and ratios of a primary drug, one or more tracer compounds, and/or relevant metabolites over a relevant period after delivery of the drug and tracer(s).

As used herein, "indirect detection" means determining the presence or concentration of a primary drug in the blood or an organ by detecting in sweat one or more tracer compounds, one or more tracer metabolites, or one or more other analytes, or through some combination of these analytes.

As used herein, "drug response profile" means the collection of sweat sensor data on sweat rate, temperature, pH, and/or analytes that indicate the chronological concentration and ratios of those analytes in the blood stream of a target individual that is correlated to the presence of a primary drug.

As used herein, "drug compliance profile" means a known set of directly detected analytes, a tracer profile and/or a response profile that is unique to compliance with a particular drug regimen.

As used herein, "drug detection threshold" means a calculated detection level in sweat of a primary drug, tracer(s), metabolite(s), other analyte(s), or a combination of these analytes that shows the primary drug is present in the blood or an organ with reasonable certainty.

DETAILED DESCRIPTION OF THE INVENTION

The ability to detect the concentration of a drug in sweat over time requires the use of a chronologically assured sweat sampling rate. To understand the proper numerical values or representations of sweat sampling rate, sweat generation rate and sweat volumes should be understood. Based on the assumption of a sweat gland density of $100/cm^2$, a sensor that is 0.55 cm in radius (1.1 cm in diameter) would cover about 1 $cm^2$ area or approximately 100 sweat glands. Next, assume a sweat volume under a skin-facing sensor (space between the sensor and the skin) of 50 μm average height or $50 \times 10^{-4}$ cm, and that same 1 $cm^2$ area, which provides a sweat volume of $50 \times 10^{-4}$ $cm^3$ or about $50 \times 10^{-4}$ mL or 5 μL of volume. With the maximum sweat generation rate of 5 nL/min/gland and 100 glands, it would require a 10 minutes to fully refresh the sweat volume (using 1st principles/simplest calculation only). With the minimum sweat generation rate of 0.1 nL/min/gland and 100 glands, it would require 500 minutes or 8 hours to fully refresh the sweat volume. If the sweat volume could be reduced by 10× to a volume height of 5 μm roughly, the max and min times would be 1 minute and 1 hour, respectively, but the min time would also be subject to diffusion and other contamination issues (and 5 μm dead volume height would be technically challenging). Times and rates are inversely proportional (rates having at least partial units of 1/seconds), therefore a short time required to refill the sweat volume can also be said to have a fast or high sweat sampling rate.

The space between the sensor and the skin could be a microfluidic component. For example, a 25 μm thick piece of paper or glass fiber covering an area of 1 $cm^2$ would equate to a volume of 2.5 μL; if the paper was 50% porous (50% solids), then the sweat volume would be 1.25 μL. With the maximum sweat generation rate of 5 nL/min/gland and 100 glands, it would require 2.5 minutes to fully refresh the sweat volume. With the minimum sweat generation rate of 0.1 nL/min/gland and 100 glands it would require about 100 minutes to fully refresh the sweat volume. "Fully refresh" is a term that in some cases should be interpreted loosely unless further details or calculations are provided. Because of mixing and diffusion over time, the moment of having a "fresh sweat volume" must be determined using finer details of the specific usage and device and situation in question.

Sweat stimulation, or sweat activation, can be achieved by known methods. For example, sweat stimulation can be achieved by simple thermal stimulation, by orally administering a drug, by intradermal injection of drugs such as methylcholine or pilocarpine, and by dermal introduction of such drugs using iontophoresis. A device for iontophoresis may, for example, provide DC current and use large lead electrodes lined with porous material, where the positive pole is dampened with 2% pilocarpine hydrochloride and the negative one with 0.9% NaCl solution. Sweat can also be controlled or created by asking the subject using the patch to enact or increase activities or conditions that cause them to sweat. These techniques may be referred to as active control of sweat generation rate.

Sweat generation rate can be measured in real time in several ways. Both sodium and chloride, which are excreted by the sweat gland during sweating, can be utilized to measure sweat generation rate in real time (higher sweat generation rate, higher concentration). Both sodium and chloride can be measured using ion-selective electrodes or sealed reference electrodes, for example placed in the sweat sensor itself and measured real time as sweat emerges onto the skin. Sato 1989 provides details on sweat generation rate versus concentration of sodium and chloride. Electrical impedance can also be utilized to measure sweat generation rate. Grimnes 2011 and Tronstad 2013 demonstrate skin electrical impedance and sweat generation rate correlations. Impedance, sodium concentration, and/or other measurements can be made and used to determine at least roughly the sweat pore density and sweat generation rate from individual sweat glands, and, when coupled with sweat sensing or collection area, can be used to determine an overall sweat generation rate to a sensor. Common electronic measurements to also predict sweat generation rate include those such as pulse, pulse-oxygenation, respiration, heart rate variability, mental activity, overall body activity level, and 3-axis accelerometry, or other common readings published by Fitbit, Nike Fuel, Zephyr Technology, and others in the current wearables field. These techniques can be referred to as measured sweat generation rate. Techniques for measured sweat rate can also be used before use of a sweat measuring device to obtain predetermined sweat generation rates for use with the sweat measuring device.

Embodiments of the present invention apply at least to any type of sweat sensor device that measures sweat, sweat generation rate, sweat chronological assurance, its solutes, solutes that transfer into sweat from skin, a property of or things on the surface of skin, or properties or things beneath the skin. Embodiments of the present invention further apply to sweat sensing devices that have differing forms including patches, bands, straps, portions of clothing, wearables, or any suitable mechanism that reliably brings sweat stimulating, sweat collecting, and/or sweat sensing technology into intimate proximity with sweat as it is generated. While certain embodiments of the present invention utilize adhesives to hold the device near the skin, other embodiments include devices held by other mechanisms that hold the device secure against the skin, such as a strap or embedding in a helmet.

Certain embodiments of the present invention show sensors as simple individual elements. It is understood that many sensors require two or more electrodes, reference electrodes, or additional supporting technology or features which are not captured in the description herein. Sensors are preferably electrical in nature, but may also include optical, chemical, mechanical, or other known biosensing mechanisms. Sensors can be in duplicate, triplicate, or more, to provide improved data and readings. Sensors may be referred to by what the sensor is sensing, for example: a sweat sensor; an impedance sensor; a sweat volume sensor; a sweat generation rate sensor; and a solute generation rate sensor. Certain embodiments of the present invention show sub-components of what would be sweat sensing devices with more sub-components needed for use of the device in various applications, which are obvious (e.g., a battery, adhesive backing, or wireless antenna), and for purpose of brevity and focus on inventive aspects are not explicitly shown in the diagrams or described in the embodiments of the present invention.

With reference to FIG. 1, a sweat sensor device 100 is placed on or near skin 12. In an alternate embodiment, the sweat sensor device 100 is simply fluidically connected to skin or regions near skin through microfluidics or other suitable techniques (not shown). The device 100 is in wired communication 152 or wireless communication 154 with a reader device 150. In one embodiment of the present invention, the reader device 150 is a portable electronic device, such as a smart phone. In alternate embodiments, the reader device is a companion transceiver is, for instance, placed at a bedside or mounted in a commercial or military vehicle. In one embodiment, the reader device 150 is a portable electronic device or companion transceiver capable of secure two-way communication with the sweat sensor device 100 and secure two-way communication with a computer network, such as a local area network or the Internet via a wireless router and/or a cellular data network. In alternate embodiments, the device 100 and device 150 can be combined. According to an aspect of the present invention, the presence or concentration of a primary drug in a bodily fluid or an organ may be determined by measuring or continuously monitoring sweat through use of a sweat sensor device and system, such as those disclosed in PCT/US2013/25092, filed Apr. 3, 2013; PCT/US2014/061083, filed Oct. 17, 2014; and PCT/US2014/061098, filed Oct. 17, 2014, the disclosures of which are incorporated herein by reference. Embodiments of the present invention may benefit from chemicals, materials, sensors, electronics, microfluidics, algorithms, computing, software, systems, and other features or designs, as commonly known to those skilled in the art.

Embodiments of the present invention may include communication techniques such as, for example, RFID or a wireless protocol such as Bluetooth, that allow the sweat sensing device to communicate with a reader device. FIG. 1 shows device 100 having a thin layer battery 160 that provides a power source for the device 100. One embodiment includes both RFID and Bluetooth used in conjunction where RFID charges a battery in the sweat sensing device when provided the proper near field communications. A device according to one embodiment may include a signal amplification mechanism to improve signal quality communicated to the reader device and to improve transmission distance to the reader device. Those skilled in the art will recognize that other biomarker sensing methods and sweat transport methods may be included in embodiments of the present invention that provide the capability of continuous or semi-continuous monitoring of biomarkers in sweat.

Embodiments of the present invention include a computing and data storage mechanism capable of sufficiently operating the sweat sensing and drug delivery system. The computing and data storage mechanism may be configured to conduct communication among system components, to monitor sweat sensor data, to perform data aggregation, to execute algorithms capable of controlling drug delivery timing and amounts, and to issue alerts and advisories related to detected analyte levels in sweat. By way of example, this computing mechanism may be fully or partially located on the sensing device, on the reader device, smart transdermal delivery device, or on a connected computer network.

The sensing and delivery system may also include data aggregation and monitoring capability. Such data aggregation may include collecting all of the sweat sensor data generated by sweat sensors and communicated to the system. Such data may also be correlated with outside information, such as the time, date, weather conditions, activity performed by the individual, the individual's mental and physical performance during the data collection, the proximity to significant health events experienced by the individual, the individual's age or gender, the individual's health history, or other relevant information.

For drug monitoring in particular, detailed information about the individual's dosage level, the drug delivery method (e.g., oral, topical, bolus injection, suppository, etc.), the timing of drug delivery, and drug delivery duration may be considered. In addition, the individual may respond to the drug differently depending on their particular genetic makeup. Further, the emergence of drugs and their metabolites in sweat may vary by individual depending on variances in how the person absorbs, distributes, metabolizes, and excretes the drug. Detailed information about the drug itself, or its metabolites, may be incorporated as well, including the drug half-life, partition coefficient (P), the dissociation constant (pK), and other relevant characteristics. Such information may also be partially supplied by an appropriately configured sweat sensor.

The reader device or companion transceiver may also be configured to correlate speed, location, temperature or other relevant data with the sweat sensor data. The data collected may be made accessible via secure website portal to allow sensing and delivery system users to perform safety, compliance and/or care monitoring of target individuals. The sweat sensor data monitored by the user may include real-time data, trend data, or may also include aggregated sweat sensor data drawn from the system database and correlated to a particular user, a user profile (such as age, gender, co-medications, drug sensitivity level, medical condition), combined analyte profile, or other relevant metric. Trend data, such as a target individual's hydration level over time, may be used to predict the likelihood of an impending physiological event. Such predictive capability can be enhanced by using correlated aggregated data, which would allow the user to compare an individual's historical analyte and external data profiles to a real-time situation as it progresses, or even to compare thousands of similar analyte and external data profiles from other individuals to the real-time situation. Sweat sensor data may also be used to identify wearers that are in need of additional monitoring or instruction, such as to adhere to a drug regimen or to avoid contraindicated drugs or behaviors. The disclosed uses of aggregated data are for illustration purposes only, and do not limit other potential sources or applications available for such data, which are within the spirit of the present invention.

A variety of pathways for delivery of a delivered solute into the body are useful in embodiments of the present invention. Delivery methods include, for example, oral ingestion, nasal, anal, transdermal absorption, and injection. A solute may also be delivered using devices or engineered products that deliver a solute into the body in a controlled or designed manner. The delivered solute may be, for example, any drug, fluid, vitamin, inert substance, salt, sugar, molecules, grains, or other suitable substance or compound.

In one aspect of the present invention, a smart transdermal delivery device communicates with a sweat sensor device such that the smart transdermal delivery device is capable of feedback control. FIG. 1 schematically shows one embodiment where the sweat sensor device 100 and a smart transdermal delivery device 200 communicate. Like the sweat sensor device 100, the smart transdermal delivery device 200 is configured with a power source 260 and a communication mechanism to enable operation. Through the communication mechanism, the device 200 is in wired communication 252 or wireless communication 254 with the reader device 150. Further, the devices 100, 200 may be configured to communicate with each other directly (line 256). The communication mechanism in particular is configured to enable communication with the sweat sensor device 100 directly, through a control device or companion transceiver, or through a computer network.

Figure 2:
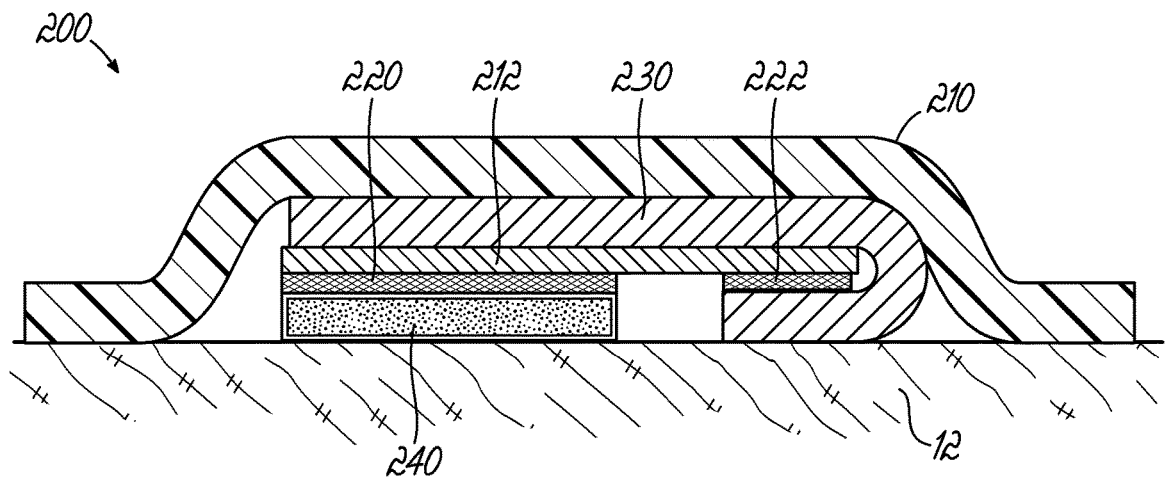
FIG. 2 is a cross-sectional view of a smart transdermal delivery device according to one embodiment of the present invention.

With reference to FIG. 2, a smart transdermal delivery patch or device 200 is placed on skin 12. The device 200 includes at least one reservoir 240 containing a substance, such as a drug and a tracer compound that are available for iontophoretic delivery, or other transdermal delivery (e.g., diffusion). The device 200 further includes electrode 220, a breathable skin adhesive layer 210, a substrate 212, and an optional microfluidic component 230. Electrode 220 may be, for example, an iontophoresis and/or electro-osmosis electrode. For example, control of electrodes 220, 222 could be computationally controlled, or controlled using simple analog electronic controls, or other suitable methods. All such control methods can be referred to as a control mechanism for controlling the dosage of one or more substances into the body. Dosage includes total amount of substance dosed into the body, the periodicity or rate, or other time or amount or other delivery factors which are important to delivery of a substance in a manner which is recommended or effective. The device 200 may also include electronics that limit activating current or total dosage to ensure harmful or toxic dosages are never reached.

In one aspect of the invention, a smart transdermal delivery device is capable of feedback control. For example, a sweat stimulating drug, such as pilocarpine or methacholine, could be iontophoretically dosed using the smart transdermal delivery device 200. The sweat sensor 100 could detect generated sweat rate by measurement of sodium concentration and/or by measurement of electrical impedance of the skin 12 and communicate that information to the smart transdermal delivery device 200. The device 200 could respond to the sweat rate information by adjusting the sweat stimulating drug delivery through a dosing electrode. This sensing and delivery system 290 could thereby control the delivery of the sweat stimulant so that it is dosed optimally to create a particular sweat rate. In another exemplary application of the smart transdermal delivery device 200, control of skin hydration could be provided. A skin hydrating cream is traditionally applied by hand, and the skin absorbs the hydrating substances by diffusion. In the present invention, the hydrating substances may be added to the microfluidic component 230 and delivered iontophoretically to the skin 12 by control with electrode 224. The hydration level of skin would be measured by the sweat sensor device 100, which could be co-located with the device such that delivery and sensing are from the same area of skin or adequately close to represent the same general area of skin. Due to the communication between the devices 100, 200, the dosing of the hydrating substance would stop once the required dose for the desired hydration level had been delivered. In another exemplary application, the smart transdermal delivery device 200 may also be used to treat inflammation. An anti-inflammatory agent such as hydrocortisone may be administered using electrode 220 from inside gel 240 into skin 12 and into muscle tissue (not shown) beneath the skin 12. The system 290 would administer the hydrocortisone based on a threshold reading from sensor 100 that indicates that muscle tissue is inflamed, for example, by detecting higher cytokine biomarker levels, which are caused by the muscle inflammation. The system 290 could then stop the anti-inflammatory dosing from device 200 once measured levels of cytokines reach a threshold level indicating less inflamed tissue.

Figure 3:
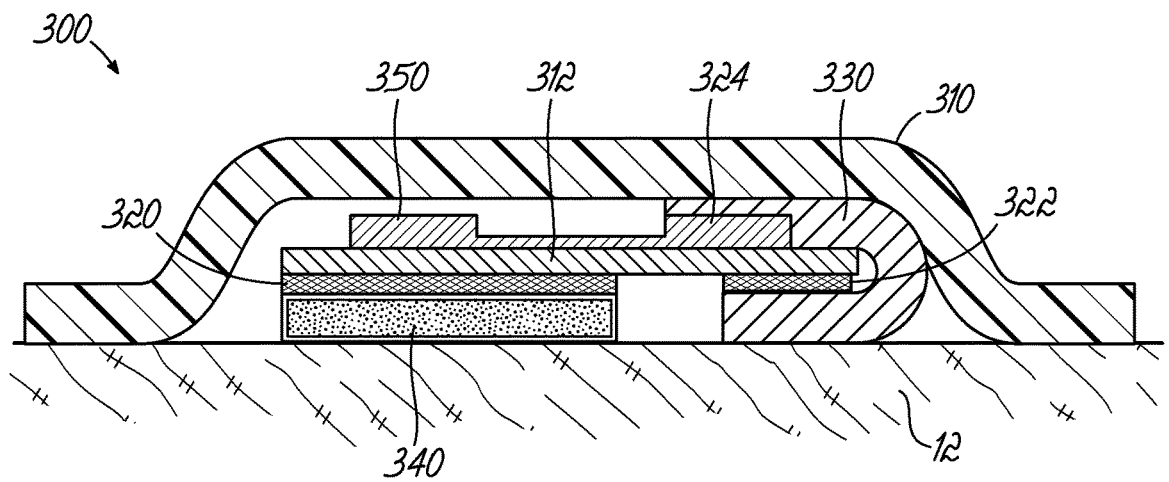
FIG. 3 is a cross-sectional view of a smart transdermal delivery device according to one embodiment of the present invention having a sweat sensing mechanism.
Figure 4:
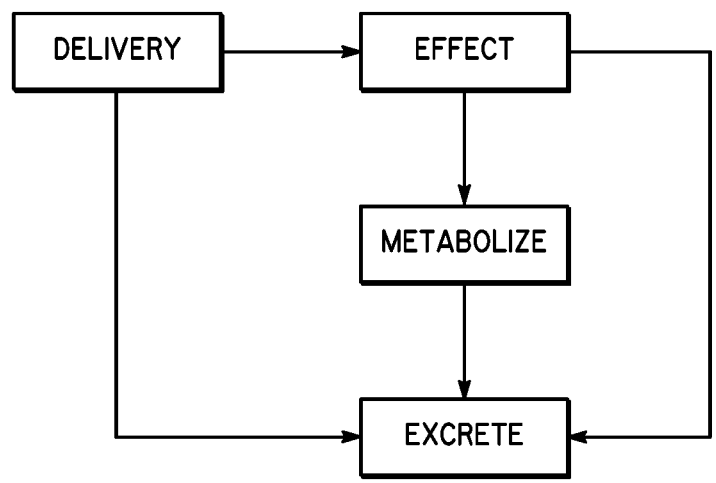
FIG. 4 is a flow diagram representing pathways a delivered solute can take before being excreted in sweat or through skin.

With reference to FIG. 3, a smart transdermal delivery patch or device 300 combines the drug delivery function and the sweat sensor function in one device. The device 300 is placed on skin 12 and includes iontophoresis and/or electro-osmosis electrode 320, impedance sensor electrode 322 for measuring sweat rate, and a breathable skin adhesive layer 310. The device 300 includes at least one sweat sensing mechanism able to perform at least one measurement of a marker for a physiological condition or response, the at least one measurement being that which would change in response to iontophoretic delivery, or other transdermal delivery (e.g., diffusion), of a substance contained in reservoir 340. The sweat sensing mechanism includes a sweat sensor 324 and electronics 350 that are carried on the substrate 312. The sweat flows from the microfluidic component 330 to the sensor 324, which is in communication with the electronics 350.

FIGS. 4-7 show flow diagrams representing pathways a delivered solute can take before being excreted in sweat or through skin in various embodiments of the present invention. With reference to FIGS. 4-7, in one embodiment, a smart transdermal delivery device capable of sensing sweat has been applied to an individual's skin. In other embodiments, a smart transdermal delivery device that is not capable of sensing sweat has been applied to an individual's skin. In such embodiments, techniques of sensing the sweat and communicating with the smart transdermal delivery device are utilized. By way of example, a sweat sensor device may also be applied to the individual's skin or a bench-top measurement system may be used to analyze the sweat. FIGS. 4-7 include the blocks 'delivery,' 'effect,' 'metabolize,' and 'excrete.' 'Delivery' represents techniques like those listed above. 'Effect' represents some biological response to the solute that is delivered. 'Metabolize' represents the body's ability to alter the delivered solute, commonly in a fashion that makes it more water soluble (but not so limited). 'Excrete' represents the delivered solute, the metabolized solute, or other analytes altered by or by effect from the original delivered solute that are excreted as sweat or through skin.

Figure 5:
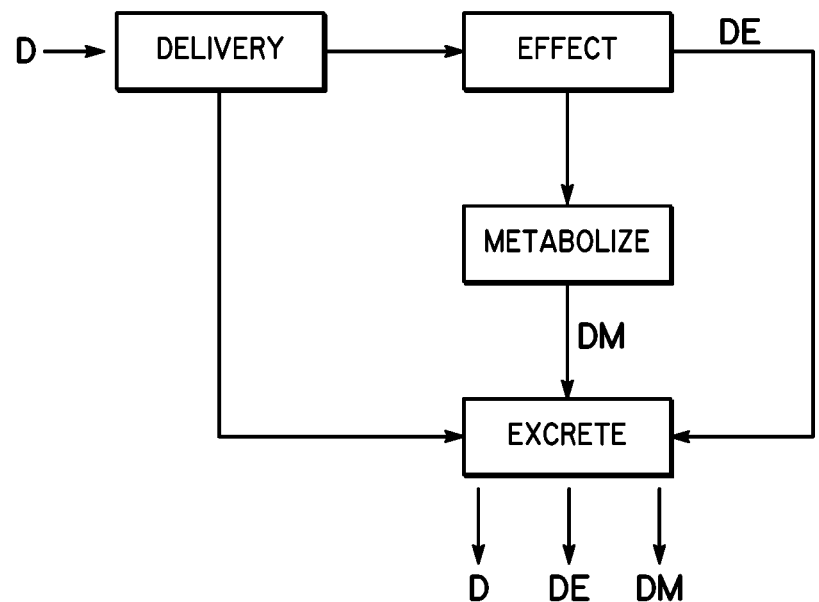
FIGS. 5-7 are flow diagrams representing pathways a delivered solute can take before being excreted in sweat or through skin according to various embodiments of the present invention

With reference to FIG. 5, an active solute is delivered, where the active solute is a drug (D). In one path, D could be directly excreted (e.g., in sweat) and sensed or measured by the sweat sensor (not shown) in its original un-metabolized form. This would allow the sensing and delivery system to detect and monitor D in sweat and utilize that to determine relevant information about the concentration of D in blood, plasma or an organ. D could also be metabolized, excreted, and then measured as a metabolite (DM). Further, since D is an active component, it has an effect on the body, and the effect could cause a change in sweat or analytes in sweat that could be measured as an effect (DE). D may also be directly detected in sweat by monitoring some combination of the un-metabolized form, the metabolized form, or the physiological effect of D, which could cause changes in other sweat or skin biomarkers or measurable aspects of sweat. Such combined monitoring may provide relevant information beyond that which can be obtained by measuring such analytes alone or independently of each other.

The ability and usefulness of directly detecting a drug in sweat will depend on the particular application, the delay between when a drug is delivered and the emergence of the drug or its metabolite in sweat, the concentration of such analytes in sweat, how the drug or the drug metabolite may become more dilute at high sweat rates, and the nature of those analytes, among other factors. The emergence of a drug or its metabolites depends primarily on the compound's partition coefficient (P) and secondarily on its dissociation constant (pK). Therefore, a compound with a high P value (high lipid solubility) will diffuse more readily from blood plasma into sweat. Similarly, a compound with a pK value close to the pH of sweat (typically about 5.0) will tend to partition into sweat more readily.

The nature of the delivered solute (e.g., the drug) or its metabolites may lend also itself more or less readily to detection by a sweat sensor. Smaller molecules, such as Na+, K+, Cl−, and other ions, are relatively easy to detect using straightforward potentiometric electrode sensors. Non-electroactive molecules often require the use of amperometric type sensors, impedance type sensors, or enzymatic type sensors, such as those based on cytochrome P450-related enzymes. Drugs with non-electroactive molecules include, for example, verapamil and benzphetamine. Larger molecules, such as proteins, are relatively more difficult to detect since they typically require the use of physical (rather than electrical) capture coatings composed of antibodies or other customized assays, which then must be read by electro-impedance spectroscopy, aptamer, optical or other methods. Other drugs simply partition into sweat in very low concentrations, requiring the use of highly sensitive and carefully-calibrated sensors. In addition, the availability of easily detected proxy molecules may also influence the decision to detect a drug directly. Consider an example involving Cystic Fibrosis treatments. When the current state-of-the art Cystic Fibrosis drugs are effectively working, the patient's sweat chloride levels will decrease to normal levels. Thus, a sweat sensor could be configured to measure sweat chloride levels to indirectly monitor the Cystic Fibrosis drug levels in the body. By this technique, the relatively more development-intensive route of detecting the drug directly may not be necessary where an easy-to-detect proxy analyte is available.

There are several drug candidates for which direct detection is recommended. For example, there are numerous diseases caused by the body's inability to regulate cortisol levels, or to generate sufficient cortisol. Therefore, cortisol supplementation in the body could be directly measured by monitoring cortisol levels in sweat. Similarly, lithium is regularly administered to control manic-depressive symptoms, yet it has a very narrow range in which it is both effective and non-toxic. Careful monitoring of plasma lithium levels is therefore required for such patients, and detection of lithium in sweat can readily be accomplished by devices according to embodiments of the present invention. In addition, certain applications, such as illicit drug or alcohol screening, might benefit from a direct detection technique.

Typically, however, drugs or their metabolites require specialized sensors to be detected. Such drugs and their metabolites emerge in sweat after a considerable lag time, such as a matter of several minutes, tens of minutes, or even longer. In these cases, the concentration of the primary drug in the body may be determined by indirect detection. One way to measure the concentration of a primary drug is by measuring the concentrations or ratios of biomarkers that are known to be affected by the primary drug. For example, rather than attempting to detect sweat insulin, which would require a specialized sensor, it might be advisable to detect sweat glucose as an indirect method of measuring the level of primary drug taken. As another example, cortisol supplementation may be revisited from an indirect monitoring method. Rather than detecting the sweat cortisol levels directly, the sweat sensor could be configured to monitor another biomarker that is regulated by cortisol and can be found in sweat, such as a cytokine biomarker. Thus, even if the concentration of a drug or its metabolites is difficult to detect directly via sweat, the drug may produce a strong and timely physiological response that may be detected indirectly in sweat.

Another method of indirect drug monitoring is enabled by administering to the patient the primary drug in combination with a known concentration of a tracer compound. The tracer compound would possess two primary desirable characteristics: 1) it ideally would be more easily detectable in sweat than the primary drug and 2) there must be a known co-relationship between the concentration of the tracer compound in sweat and the concentration of the primary drug or its metabolite in either an organ or in a bodily fluid (e.g., blood, plasma, or serum). The tracer compound may also be a) useful for detection by the sweat sensor, even at low concentrations, b) non-toxic, and c) relatively inactive in the body.

Figure 6:
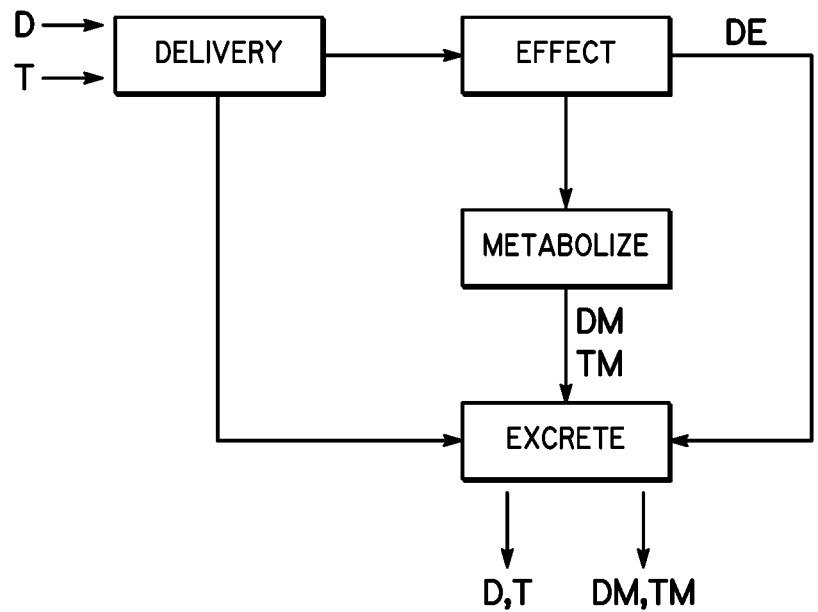

With reference to FIG. 6, an inactive delivered solute, a solute less active than the primary delivered solute, a solute that is differently active from the primary delivered solute, or a tracer compound (T) is delivered along with D. T has the purpose of helping track or measure the body response to D, or the concentration of D in the body, or the concentration of the metabolites DM of D in the body. T could be a molecule that is soluble at the same or predictable levels to D, or which metabolizes similarly or predictably to that of D. T can therefore be used to predict effects, concentration, circulation, and other aspects of D by measuring T or its metabolites (TM) instead of D. A particular advantage of the use of a tracer compound is that T may be specifically selected to enable a strong or otherwise informative reading by a sweat sensor, for example, T may partition more predictably or rapidly from the body into sweat, or it may be safely administered at higher concentrations, such that it appears at a high concentration in sweat. Furthermore, T could be specifically molecularly designed to work well with a particular sweat sensing modality. In addition, D and T and/or their metabolites DM, TM could also be measured to increase the value of data or measurements obtained by the sweat sensor. In a further embodiment, D may represent a placebo. In this manner, the tracer compound T may be used in a clinical trial setting. Measuring T or its metabolites TM may be useful to monitor a participant's compliance with the placebo regimen and to ensure uniform conditions for the clinical trial.

In one embodiment, T is a compound that would be metabolized in the body in generally the same manner as D or metabolized at a known correlated rate as D. For example, if D is metabolized through the liver, then T would also be a compound that is metabolized through the liver. Precisely determining the chronological concentrations of D and T in a relevant fluid (e.g., sweat, blood, or plasma) or a relevant organ (e.g., the kidneys or liver) or the chronological ratios of the compounds D, T or their metabolites DM, TM to each other, allows the use of a tracer compound to further enable or enhance the detection of D via the sweat sensor.

In one aspect of the present invention, the use of a tracer compound to enhance the detection of the primary drug may be further enhanced by prior testing to determine a tracer profile or chronological relationship between tracer compound(s) and a particular primary drug as they proceed from delivery into the body to excretion in a relevant fluid, such as sweat or plasma. The drug tracer profile could include a process to determine the relationship between the primary drug and the tracer candidate. The primary drug and a tracer candidate are delivered into the body, and a sweat sensor (either via sweat sensor device or by lab instrument) is used to monitor the individual's sweat over the half-life of the drug or other suitable interval. The sweat sensor may be configured to monitor the chronological profiles of a number of relevant substances, to include the primary drug, one or more tracer molecules, and/or metabolites of these substances. By monitoring the selected substances in sweat over time, the tracer profile would be developed to contain detailed information about the concentrations and ratios of the various analytes over time as they are processed in the body. Alternative, less costly, processes could also be employed by limiting the number of analytes monitored during the testing process. For example, after administering the primary drug and the tracer candidate, only the tracer's chronological profile in sweat might be monitored. In this way, a precise chronological profile of the tracer in sweat as affected by the primary drug may be developed, which, with sweat sensor algorithms, can then be used to enhance the use of the tracer compound to indirectly monitor the primary drug.

Figure 7:
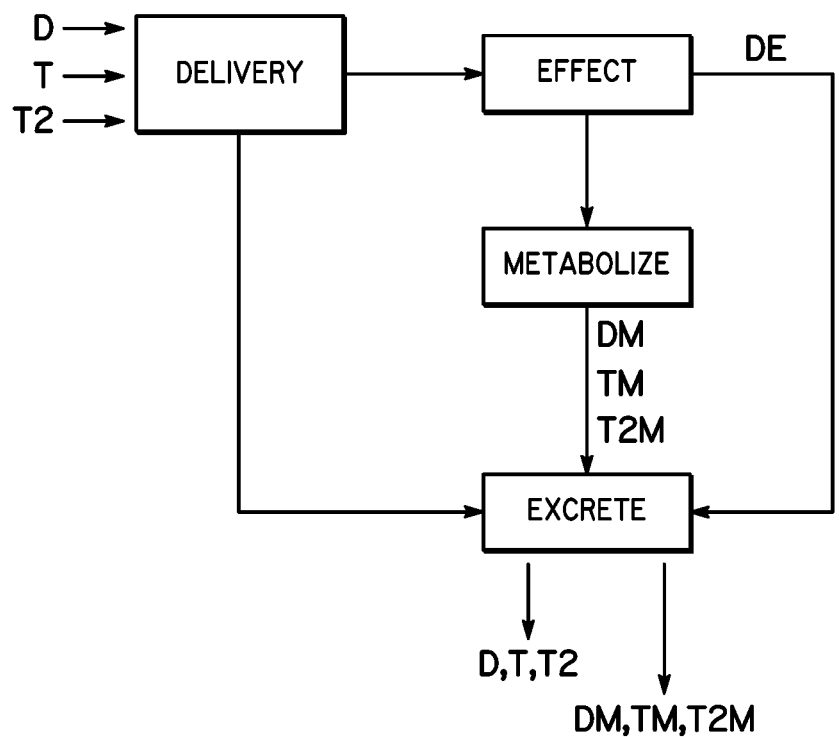

With reference to FIG. 7 a second tracer solute T2 is added, which can provide benefits similar to those gained by using T. Further, additional tracers may also be administered (i.e., T3, T4 . . . $T_n$) to enhance the capabilities of the sensing and delivery system to indirectly detect and monitor D. The additional tracer compounds can be active or inactive, as long as they are compounds that are deemed adequately safe and which provide advantages over attempting to sense D alone. As with D and T, these additional tracer compounds may have their one-time or chronological concentrations in sweat monitored individually, or the ratios among the various tracers and the primary drug, or metabolites thereof, could be monitored chronologically.

In a further embodiment of the invention, the individual may be administered one or more tracers, which metabolize in the body at different rates. Solutes that are highly water-soluble are typically excreted in sweat relatively quickly after delivery compared to less soluble compounds. Further, as solutes metabolize, their metabolites may become predictably more water-soluble. Therefore, tracer compounds may be selected that have known and predictable post-delivery excretion periods. In this way, a tracer that metabolizes very slowly or which has low water solubility, may be measured to represent the amount of D appearing in blood initially after delivery. A tracer that metabolizes very quickly or which is already highly water-soluble may be used instead to show the rate at which a metabolite (DM) of D is excreted through urine, or the rate at which D reaches the bloodstream if D and the tracer have similar partition rates into blood. Such use of tracer compounds could therefore allow the determination of (1) initial D dosage in plasma; (2) rate of D passage into sweat, kidneys or other organs; and (3) active remainder of D in plasma over time, among other things.

Co-administration of a tracer compound necessitates that this tracer compound also be FDA approved, generally regarded as safe ("GRAS"), or monographed (e.g., aspirin). Accurate knowledge of the tracer compound's pharmacokinetic profile will allow it to be correlated with appropriate drugs of interest. Chiefly, this will involve matching the two substances' metabolic pathway and/or the time profile between delivery and excretion. One potential limitation for FDA-approved tracer compounds is that such compounds likely have some degree of pharmacological activity to be classified by the FDA. As a result, the tracer compound's active property must be one that is rather inconsequential or non-interfering with the drug of interest (e.g., does not block CYP activity).

One such candidate tracer compound is the well-known drug ibuprofen, which has an active and an inactive stereoisomer. The active stereoisomer, S-ibuprofen, is frequently used as a primary drug for treatment of pain or inflammation. Like S-ibuprofen, the inactive stereoisomer R-ibuprofen possesses a similar metabolic path through the liver and has similar water solubility. Ibuprofen has a relatively short half-life in the body of 1.3 to 3 hours. It is also safe for use in the body and causes no known serious side effects. It can therefore be co-administered with the active S-ibuprofen as a tracer compound. The system could then be used to determine the concentration of S-ibuprofen indirectly by monitoring the concentration of R-ibuprofen metabolites, such as 1- and 2-hydroxyibuprofen, or 1- and 2-hydroxyibuprofen glucuronide, in sweat. The system may also enhance its direct detection of S-ibuprofen by detecting and analyzing the concentration ratio of R-ibuprofen to S-ibuprofen, which may provide a more accurate measure than measuring S-ibuprofen metabolites alone. Similarly, R-ibuprofen may be used as a tracer compound for other active drugs, such as opiates, antibiotics, lidocaine, glucocorticoids, and other compounds that are also hepatically metabolized. Other NSAID compounds with similar P and pK values (e.g., indoprofen, diclofenac, naproxen, and sulindac), may also prove to be effective tracer compounds. Para-aminobenzoic acid (PABA) may also be a suitable tracer compound. Similarly, S-ibuprofen could be used as a tracer compound for other active drugs.

None of the cases discussed above are necessarily perfect matches between drug and tracer metabolic profiles. The cases are given as examples to further illustrate aspects of the present invention. Further examples are listed as adopted from Chhabra et al., 2013, "A review of drug isomerism and its significance." Pharmacodynamic differences resulting out of stereoisomerism can affect pharmacological activity and potency. For instance, 1-Propranolol has beta-adrenoceptors blocking action while d-propranolol is inactive. Carvedilol is a racemic mixture, where the S(−) isomer is a nonselective beta-adrenoceptor blocker, while both S(−) and R(+) isomers have approximately equally alpha-blocking potency. S-Timolol is more a potent alpha-blocker than R-timolol but both are equipotent ocular hypotensive agents. Labetalol is formulated as a racemic mixture of four isomers, two of these isomers—the (S, S) and (R, S) isomers—are relatively inactive, while the (S, R) isomer is a potent alpha-blocker and the (R, R) isomer is a potent beta-blocker. Labetalol has a 3:1 ratio of beta to alpha antagonism after oral administration. Sotalol is formulated as a racemic mixture of D- and L-isomers where the L-isomer has beta-blocking activity, while the D-isomer has no beta-blocking activity. Nebivolol has highly selectively beta-1-blocking effects, while the L-isomers causes vasodilatation. Most beta-2-selective agonist drugs are formulated as a racemic mixture of R- and S-isomers. Only the R-isomer of the beta-2-selective agonist drug has the beta-2-agonistic activity, while S-isomer has no beta-2-agonistic activity and even promotes inflammation. Salbutamol is available as a single isomeric preparation of R-isomer as levalbuterol. Halothane, enflurane, and isoflurane are chiral drugs with different anesthetic potencies. D-(+) 2R,3S propoxyphene is analgesic while (−) 2S,3R propoxyphene has antitussive action.

Dextromethorphan (DXM or DM), an antitussive (cough suppressant) drug, is another possible tracer compound. It is one of the active ingredients in many over-the-counter cold and cough medicines, including brands such as Benylin DM, Mucinex DM, Robitussin, NyQuil, and related generic labels. While at high doses, Dextromethorphan may cause dissociative hallucinogenic effects, it is a well-studied compound that, at the doses useful in embodiments of the present invention, is regarded as safe and has relatively mild active properties. DM has a half-life comparable to that of ibuprofen at about 2-4 hours.

Antimicrobials represent another class of candidate tracer compounds that are safe and possess useful properties for sweat monitoring. For example, quinolone antimicrobials may be transferred into sweat. This is a well-studied group of molecules with known pharmacokinetics and excellent existing analytical methods for determining levels in biological fluids. Quinolones generally have low metabolism rates and, hence, longer half-lives in the body. Exemplary candidates from this class include Ciprofloxacin, Levofloxacin, Gatifloxacin, Ofloxacin, or Moxifloxacin. Similarly, Beta Lactam antimicrobials, such as Ceftriaxone, ceftazidime, and cefuroxime, have been studied in sweat, and also tend to have long plasma half lives with modest metabolism rates.

Anti-fungal medications, such as Ketoconazole and Fluconazole, represent another class of drugs that contains candidate tracer compounds. These drugs are known to be excreted into sweat, are well studied, have established analytical methods for determining their concentrations in biofluids. These compounds have modest metabolic rates and relatively innocuous side effect profiles.

Nicotine has also been measured in sweat of smokers and non-smokers and has also been well studied in dermal indications through its use in transdermal delivery patches. Nicotine has a short half-life of about 1 to 2 hours, and its metabolite cotinine has a much longer half-life of about 20 hours. Nicotine and cotinine therefore may be useful tracer compounds for numerous drug monitoring applications across a broad time range.

Finally, tocotrienols, which are members of the Vitamin E family of compounds, form another class of candidate tracer molecules. This class of tracer compound presents some challenges that may be typical in the selection of tracer compounds for sweat sensor applications. Vitamin E is made up of four tocopherols (α-, β-, γ-, δ-) and four tocotrienols (α-, β-, γ-, δ-). Tocotrienols and tocopherols are very similar in structure and are featured in many natural substances, including rice bran oil, palm oil, wheat germ, barley, saw palmetto, annatto, and certain other types of seeds, nuts, grains, and derivative oils. Of the two sets of compounds, tocotrienols are better candidates for tracer molecules, since they typically are found in low concentrations in nature. Since natural food sources are light in tocotrienols (e.g., an individual would have to consume 1 kg (2.2 lbs) of olive oil to ingest just 93 mg of tocotrienols) few foods would spike tocotrienol levels at the same rate as a pill administered orally. Further, unlike a pill, foods must be digested, so the absorption rate of tocotrienol into the bloodstream from food is lower. Tocotrienol concentrations in sweat are therefore less likely than tocopherols to be skewed by an individual's diet if they are delivered as a tracer compound.

The selection and use of tocotrienol as a tracer molecule also depends on whether a useful amount of the tracer molecule for sweat sensing can be delivered without causing unwanted side effects. Vitamin E, in high concentrations, can act as an anticoagulant, increasing the risk of bleeding problems. As a result, many agencies have set a tolerable upper intake levels (UL) at 1,000 mg (1,500 IU) per day. Currently, the U.S. Food and Drug Administration has set standards only for intake of α-tocopherol, but not the other Vitamin E family compounds. Nevertheless, the 15 mg adult Recommended Daily Allowance (RDA) of α-tocopherol may be taken as a benchmark. For example, a dose of 500 mg would be sufficient to allow tocotrienol to function as a tracer molecule for most sweat sensor applications. Therefore, delivering 500 mg of tocotrienol would present the body with concentrations not likely to be seen in daily life, and the amount would not be high enough to cause serious side effects. Tocotrienol is therefore a strong candidate for an effective tracer compound.

The Vitamin E family of compounds also metabolizes into potentially useful tracer molecules such as, for example, carboxyethyl-hydroxychroman (CEHC). Many of the candidate metabolites can arise from any form of Vitamin E, so more careful attention must be paid to the Vitamin E concentration of foods in general to successfully do so. However, most foods have only about 10 to about 100 mg/kg of Vitamin E, so administering 500 mg of Vitamin E would result in higher metabolite concentrations than would normally be seen in daily life, again without causing serious side-effects.

Metabolites of Vitamin E show up in body fluids such as urine at about 1% to about 10% of the orally administered Vitamin E, which is an easily detectable concentration. Unfortunately, measuring metabolites in urine lags the levels found in blood by several hours. Additionally, the chronological monitoring capability of urine is poor without the use of a painful catheter. Unlike urine, however, metabolites of Vitamin E, like CEHC, emerge relatively rapidly in sweat after ingestion. Dye clearance tests show that CEHC, and other highly water soluble molecules, are excreted in sweat with a resolution of about 2-3 minutes. Therefore, CEHC would also be a superior tracer compound for use in sweat.

The half-lives of Vitamin E family compounds are in the ranges of about 2-4 hours, and more specific half-lives can be achieved if a particular form of Vitamin E is delivered in isolation from other types of Vitamin E (such as α- or β-tocotrienol). Further, the sweat sensor could be configured to monitor combinations of the Vitamin E compounds and their metabolites as tracer molecules to improve the system's ability to indirectly mimic and trace the similar kinetics of a primary drug.

PEGylated drugs may also present several candidates for tracer compounds. PEGylated drugs are altered by bonding various polyethylene glycol (PEG) polymer chains to improve water solubility and decrease the rate of metabolic processing by the kidneys. As these PEGs are metabolized, they emerge in sweat to be detected by the system. A particular advantage of such compounds is their GRAS status, and the pharmacological profiles of these substances are well-known. Numerous drugs could therefore be monitored by the use of tracer compounds, as the half-lives of several drugs and drug types are well known in the art.

CEHC, for example, may be detected by use of electrochemical immunosensor. An initial requirement for this type of sensor is a protein, such as an antibody, capable of binding with the molecule. Neither the antibody or aptamer (BRE) for γ-CEHC is commercially available, but one could be developed if required. The immunosensor signal originates from enlarged and positively charged gold nanoparticle (AunP)-mediated electron transfer between an insulating self-assemble monolayer (SAM) modified electrode and a $K_3Fe(CN)_6$ solution. The AunP electrode is first modified with SAM to block the electron transfer between the electrode and $K_3Fe(CN)_6$ solution. After the preparation of the immunosensor, the AunPs attached to the electrode are enlarged and positively charged by treating them in a solution containing $HAuCl_4$, ascorbic acid, and acetyltrimethylammonium bromide (CTAB). The enlarged and positively charged AunPs then mediate electron transfer between the electrode and $K_3Fe(CN)_6$ solution, creating a redox current that is proportional to the concentration of γ-CEHC detected. This immunosensor can be highly sensitive and have a wide linear range for this type of analyte.

In addition to using tracer molecules to indirectly monitor a primary drug, devices according to embodiments of the present invention can also use correlated aggregated sweat sensor data to indirectly monitor the presence of a primary drug in the body by detecting and monitoring biological responses to the drug, such as changes in sweat rate, or concentration trends and ratios of analytes correlated with the presence of the drug.

Similar to the use of a tracer profile, as detailed above, a device according to an embodiment of the present invention could also be configured to monitor a drug response profile, or the physiological responses to a primary drug in the form of analyte concentrations, analyte ratios, or trend data. For example, a smart transdermal delivery device and/or a sweat sensor may have access to aggregated data on a particular individual or other individuals of similar age that have taken a particular primary drug. Through this aggregated data, the sweat sensor would develop a response profile that typifies the physiological response to the presence of a primary drug. This response profile may be customized to various levels for a particular individual, to include relevant criteria such as age, liver function, kidney function, fitness level, and etc. It also may be customized to include other factors, such as hydration level, activity level, or environmental conditions. The sensing and delivery system could use the aggregated data to determine whether the detected analytes from a sweat sensor match the response profile that corresponds to adherence to a drug regimen. Such a response profile may be developed through prior testing.

Embodiments of the present invention include and can benefit from the employment of various combinations of direct and indirect detection of a primary drug, the effect of a primary drug on existing biomarkers, the use of tracer compounds, and various combinations thereof. In one embodiment, therefore, a sweat sensor device may be internally configured to detect the primary drug and its metabolites, a tracer profile and/or a response profile in a combined drug compliance profile. The drug compliance profile would consist of analytes that, when taken together, indicate with high probability that a test subject has taken the drug or is, or is not, following a drug regimen. A compliance profile for a particular drug may be predicted using correlated aggregated sweat sensor data, or it may need to be developed by prior testing.

In one embodiment, the sensing and delivery system could be configured to use a drug detection threshold, or calculated detection level of a primary drug, a tracer compound, a metabolite, or a combination of these analytes, that shows that the primary drug is present with reasonable certainty. The drug detection threshold may be used in single-use scenarios, or may be calculated for continuous use scenarios. In an exemplary embodiment, a process could be implemented to determine the relationship between the primary drug and the tracer candidate. Known amounts of the primary drug and a tracer candidate are delivered into the body, and a sweat sensor is used to measure the individual's sweat over an interval sufficient to take a meaningful reading. The sweat sensor may be configured to detect the presence of the primary drug, one or more tracer molecules, and/or metabolites of these substances. The drug detection threshold may be calculated using aggregated sweat sensor data correlated with relevant external data. In this way, a precise threshold for detecting the primary drug may be developed that considers the patient's individual characteristics, details about their drug regimen, such as the amount of time they have taken the drug, and other relevant information. By using sweat sensor algorithms, these thresholds can then be used to enhance the ability of the system to detect the presence of the primary drug.

The ability to detect and/or chronologically monitor the concentration of a drug in the body with the sensing and delivery system described herein has several potentially useful applications. It can be used, first of all, to determine whether a patient has taken his or her medication, or has taken it according to the required regimen. Embodiments of the present invention as described may also be used to provide individualized measurement of toxicity response to particular medications by comparing an individual's detected response to known variances across various health populations through correlated aggregated sweat sensor data. Such drug monitoring may also be used to manage organ transplant rejection by carefully monitoring the levels of anti-rejection medication along with detected indications of organ rejection, such as increased levels of inflammatory response molecules, like interleukin 10, for instance. The invention as described may also be used to enhance cardiac stress tests by using a delivered solute to track a targeted or system-level response to the stress test. Multiple applications are possible, and are contemplated within the present invention.

Utilizing the ability to determine the concentration of a primary drug in an individual's body, the system can use feedback, perhaps in combination with correlated aggregated sweat sensor data, to control the delivery and dosage for the primary drug through a smart transdermal delivery device described above. The smart transdermal delivery device may be situated on the same patch as the sweat sensor, or may be on its own wearable patch. Feedback control may be accomplished by various mechanisms via the smart transdermal delivery patch, including controllable microfluidic gates, iontophoretic electrodes, and heat assisted diffusion, among others.

In one embodiment, the feedback control capability of the sweat sensor working in conjunction with such a transdermal delivery device could ensure a drug was administered only when needed. A transdermal drug compound containing lithium could be delivered into the body by diffusion to control schizophrenia. In one embodiment, the introduction of the drug to skin and therefore diffusion and delivery is regulated by microfluidic gates or another type of gate controlled by the sensing and delivery system. In one embodiment, the gate could be controlled by electrowetting using techniques known by those skilled in the art. The gate could also be an electro-active polymer which swells in response to electricity and which closes off a microfluidic channel as known by those skilled in the art of microfluidics. In one embodiment where the drug is charged, the drug could be electrically introduced near the skin surface through a track-etch membrane since the porosity of the membrane is very low, which substantially blocks diffusion of the drug, but through which current driven transport of the drug could be very high. The system measures and interprets biomarkers for increased risk of a schizophrenic episode and releases the drug accordingly. In another example, the transdermal patch alone might be used to apply the correct dosage of a numbing agent. A numbing drug, such as lidocaine, could be loaded into a smart transdermal delivery device and placed on the skin. The device would administer the drug by iontophoresis and could also apply an electrical stimulus to the skin and muscle to determine numbness. The device would also include a strain sensor or other mechanisms to determine when the skin or muscle no longer twitches in response to the stimulus. Once the skin or muscle no longer responds, the device would determine that the lidocaine has been correctly dosed. The device could then periodically monitor for skin response, and if muscle twitches are later detected, numbing agent could again be administered.

The device could also benefit from various methods known to those skilled in the art to control, facilitate, or improve the delivery of substances into the skin by the smart transdermal patch. In various embodiments, the patch may employ the following delivery enhancement methods that can be tuned in response to sweat sensor feedback, such as: iontophoretic delivery, electroporation, microneedle arrays, or dispensing solvents, such as glycols or oils, that increase or decrease skin permeability to the drug. Solvents that increase skin permeability could be stored in a reservoir or other fluid storing material until dispensed onto the area of skin for transdermal delivery. In other embodiments, a smart transdermal patch may include a drug reservoir that is gated using microfluidic gates known by those skilled in the art. The device may also vary the concentration of drug delivered to the skin's surface, since a higher concentration of available drug generally results in a higher concentration of the drug diffusing into the body. Other embodiments of the transdermal patch may use heat, which can change capillary flow or swelling at the site to change skin permeation or drug permeation rate. At higher temperatures, the diffusion rate of any substance typically increases. Components used to provide heat can include, for example, those found in commercial chemical heat packs (e.g. hand warmers), thin film printed electrical resistor heaters, or other suitable methods that provide heat on demand as needed to control transdermal delivery. Other suitable methods known by those skilled in the art are also available and are contemplated in the present invention. Embodiments of the present invention also include a drug delivery component that could be in the mouth, implanted in the body, suppository, or other suitable method for controlled drug delivery.

In an advantageous aspect of the present invention, the measured biomarkers or analytes could also be electro-osmotically extracted for some applications or simply allowed to diffuse out of skin, sometimes directly to a detector, sometimes into sweat. In addition to measuring drug or substance metabolites, biomarkers, or other analytes in sweat, skin or other properties known in the art may be measured using mechanical, chemical, optical, or other suitable methods to provide the data to enable feedback control in the smart transdermal delivery patch.

Figure 8:
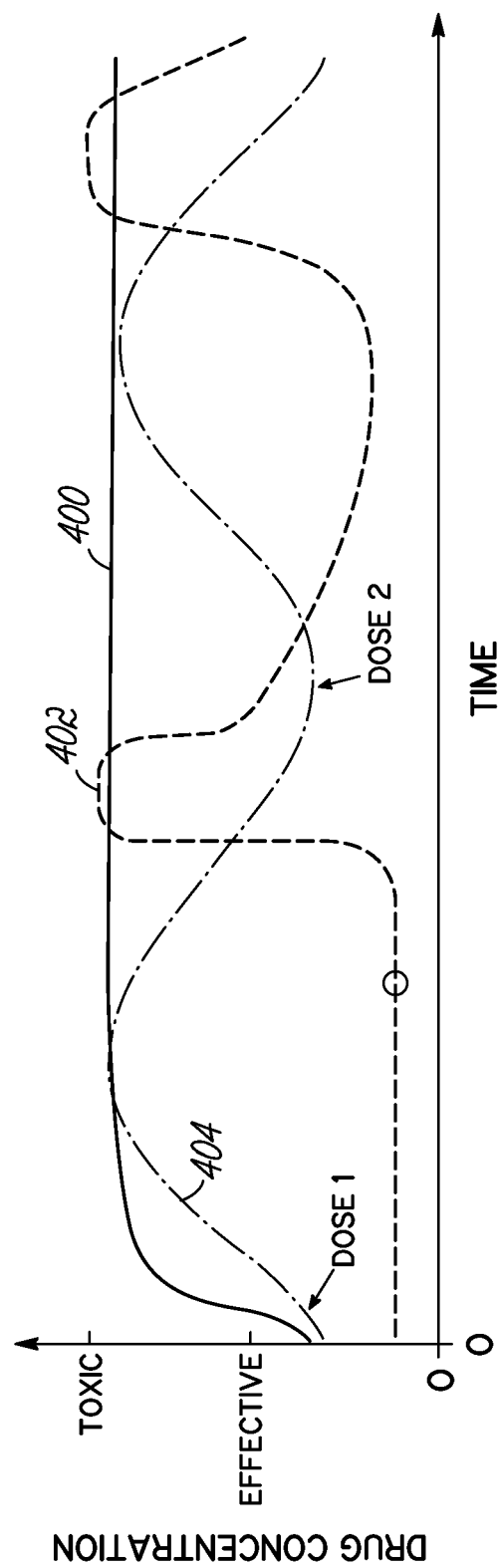
FIG. 8 is a chart showing the relationship of drug concentration over time using various methods of administering the drug.

With reference to FIG. 8, generally the smart transdermal patch would have advantages compared to standard oral dosing. Lines 400, 402 represent a regulated dosing of a drug using embodiments of the present invention. The standard oral dosing line 404 shows two dosing events. The 'effective' and 'toxic' levels of the drug concentration in blood are also labeled. Embodiments of the present invention could regulate the maximum safe or maximum needed dosage (400). Compared to standard oral dosing (404), a regulated dose based on continuous feedback from a sweat sensor device has a reduced chance of causing an overdose. For example, patients frequently overdose on oral painkillers because they experience a decrease in effectiveness, which would not occur with a system-regulated dosing schedule. The smart transdermal patch could be used to dose a primary drug only as needed (402), for instance, in an application where a patient experiences heart arrhythmia and rapid dosing of a medication is needed, but the medication's side effects make it undesirable for frequent or continuous use. In an aspect of the present invention, compliance monitoring and automatic dosing may also provide superior adherence with a drug regimen.

In addition to the above, devices according to the present invention as described above may be found beneficial in other industrial applications. Exemplary applications are discussed below. Those of ordinary skill in the art will recognize how to modify or configure a device according to an embodiment of the present invention so as to effectively operate in these other applications. Thus, the various features of the invention may be used alone or in numerous combinations depending on the needs and preferences of the user.

In one embodiment, a sweat sensor device may be used to improve a physician's ability to distinguish between viral and bacterial pneumonia. A patient may present to the doctor with pneumonia, but the proper course of treatment would depend on the nature of the infection. The physician could deliver a particular solute to the patient's lungs via inhalation. The solute would be selected, for example, because it is readily metabolized by bacteria. When the solute partitions into the blood through the lungs and is detected by the sweat sensor, the detected metabolite(s) would indicate whether the infection is bacterial. When the physician interprets the sweat sensor data, it shows levels of the metabolite exceeding a calculated threshold, indicating a bacterial infection. The doctor therefore concludes that the infection is likely bacterial and prescribes a suitable course of antibiotics.

A patient experiencing chronic pain is prescribed an opiate painkiller. The opiate is administered orally along with an S- or R-ibuprofen tracer or a mixture thereof. When the drug is administered, a sweat sensor device according to an embodiment of the present invention configured to monitor ibuprofen and its metabolites is placed on the patient. The sweat sensor activates, conducts initialization and establishes communication through the Internet with the delivery system. The system conducts a baseline reading for ibuprofen and one or more metabolites in sweat, and then begins to continuously monitor for those analytes. Based on a calculated tracer profile, and correlated patient information, the system determines that a specific concentration of ibuprofen and the metabolite(s) corresponds to an adequate dosage of the opiate. After several hours of monitoring, the system determines that the opiate dosage level is low, and alerts the patient's caregiver that additional dosage is recommended. The patient therefore receives better pain control without receiving excessive amounts of the opiate.

An individual with hyperglycemia is prescribed a sweat sensor device and transdermal delivery patch device according to an embodiment of the present invention for blood glucose control. The individual is given a kit with sweat sensor devices for a number of days, smart transdermal delivery patches, and skin cleaning swabs. The kit also contains a companion transceiver that communicates with the Internet. The sweat sensor devices are configured to detect sweat rate, glucose, and cortisol levels in sweat. The smart transdermal delivery patch is equipped with a reservoir of insulin and an iontophoretic delivery mechanism. At night before sleep, the individual puts on a sweat sensor device and a delivery patch. During the night, the sweat sensor device detects high glucose levels, and communicates this to the sweat sensor device and the delivery patch. The delivery patch activates the iontophoresis circuits and transdermally administers an appropriate dose of insulin. The sweat sensor continues to monitor and finds glucose levels have been restored within selected parameters.

In another exemplary embodiment of the present invention, the sweat sensor may be used to determine whether a patient has received an optimal dose of a drug. Drug efficacy varies depending on individual genetic phenotypes, pharmacokinetics, and drug metabolism rates. Such considerations are particularly important for psychotropic drugs like fluoxetine, sertraline, venlafaxine, duloxetine, imipramine and others, which have known variances in efficacy depending on individual phenotypes. In addition, the sweat sensor will also account for individual differences in sweat sensor data caused by individual variances in absorption, distribution, metabolism, and excretion of the drug. The sweat sensor could be used to monitor drug levels over time after administration, accounting for these individual variances and discerning overall dosage, timing and magnitude of peak and minimum sweat concentrations, and drug half-life to assist in determining a dosage required to provide the blood concentration profile associated with optimal drug effectiveness and safety. Alternatively, the sweat sensor may use such readings to characterize an individual's pharmacokinetic profile for a particular drug. This approach will aid administration of drugs that are prone to abuse, such as opioid pain relievers, as well as drugs with a narrow range in which they are both effective and non-toxic, such as oral chemotherapeutics.

This is a description of the present invention, along with the preferred method of practicing the present invention and the invention itself should be defined only by the appended claims.

What is claimed is:

1. A method comprising:
    administering to a patient a known amount of a primary drug;
    administering to the patient a known amount of a tracer;
    using a sweat sensing device to take a plurality of measurements of solutes in sweat at a sampling rate having a chronological assurance, wherein the solutes include the tracer or a metabolite of the tracer;
    receiving a tracer concentration, wherein the tracer concentration is a concentration of the tracer in sweat or a metabolite of the at least one tracer in sweat; and
    correlating the tracer concentration with a concentration of the drug in the patient's blood or an organ, wherein a sweat to blood correlation includes one of the following: a time of administration of the drug, a time of administration of the tracer, a method of administration of the drug, a method of administration of the tracer, and a time of detection of the tracer concentration.

2. The method of claim 1, wherein detecting the tracer concentration further includes measuring one of the following in sweat: the drug, at least one metabolite of the drug, or an analyte.

3. The method of claim 2, wherein correlating the tracer concentration with a concentration of the drug further comprises identifying a relationship among concentrations in sweat of two or more of: the drug, a metabolite of the drug, the tracer, a metabolite of tracer, and the analyte.

4. The method of claim 1, wherein the tracer is metabolized in a known rate correlated to the drug.

5. The method of claim 1, wherein correlating the tracer concentration with a concentration of the drug occurs more than once.

6. The method of claim 1, wherein correlating the tracer concentration with a concentration of the drug includes at least one of the following: a characteristic of the patient and a biological response to the primary drug by the patient.

7. The method of claim 1, wherein correlating the tracer concentration with a concentration of the drug includes at least one of the following: a half-life of the tracer, a partition coefficient of the tracer, a dissociation constant of the tracer, and a size of the tracer.

8. The method of claim 1, wherein correlating the tracer concentration with a concentration of the drug includes at least one of the following: a half-life of the drug, a partition coefficient of the primary drug, a dissociation constant of the drug, and a size of the drug.

9. The method of claim 1, further comprising correlating the concentration of the drug to a concentration of the drug in a population to characterize an individual variance of the patient.

10. The method of claim 2, wherein correlating the tracer concentration with a concentration of the drug includes identifying a relationship among sweat concentration changes over time two of: the drug, a metabolite of the drug, the tracer, a metabolite of the tracer, and the analyte.

11. The method of claim 1, further comprising:
    administering to the patient a known amount of a second tracer;
    using the sweat sensing device to take a plurality of measurements in sweat of the second tracer or a metabolite of the second tracer at a sampling rate having a chronological assurance;

wherein the tracer concentration further comprises a concentration of the second tracer or a metabolite of the second tracer in sweat; and wherein the sweat to blood correlation further includes one of the following: a time of administration of the second tracer, and a method of administration of the second tracer.

* * * * *

UNITED STATES PATENT AND TRADEMARK OFFICE
CERTIFICATE OF CORRECTION

PATENT NO. : 11,129,554 B2
APPLICATION NO. : 15/314414
DATED : September 28, 2021
INVENTOR(S) : Jason Charles Heikenfeld It is certified that error appears in the above-identified patent and that said Letters Patent is hereby corrected as shown below:

On the Title Page

Column 1, page 3, item [56], Line 29, "dispostion" should read --disposition--.

Column 1, page 5, item [56], Line 20, "Tectiles" should read --Textiles--.

In the Specification

Column 3, Line 59, "area, which provides" should read --area provides--.

Column 3, Line 62, "require a 10 minutes" should read --require 10 minutes--.

Column 13, Line 24, "isomers causes" should read --isomers cause--.

Column 14, Line 35, "upper intake levels" should read --upper intake level--.

In the Claims

Claim 3, Column 20, Line 32, "metabolite of tracer" should read --metabolite of the tracer--.

Claim 6, Column 20, Line 41, "the primary drug" should read --the drug--.

Claim 8, Column 20, Line 50, "the primary drug" should read --the drug--.

Claim 10, Column 20, Lines 58-59, "over time two of" should read --over time of two of--.

Signed and Sealed this
Twenty-eighth Day of December, 2021

Drew Hirshfeld
*Performing the Functions and Duties of the
Under Secretary of Commerce for Intellectual Property and
Director of the United States Patent and Trademark Office*